(12) United States Patent
Lang et al.

(10) Patent No.: US 7,790,742 B2
(45) Date of Patent: Sep. 7, 2010

(54) SUBSTITUTED 4-PHENYLTETRAHYDROISOQUINOLINES, PHARMACEUTICAL COMPOSITIONS THEREOF, METHODS FOR THEIR PREPARATION AND THERAPEUTIC USE

(75) Inventors: Hans-Jochen Lang, Hofheim (DE); Uwe Heinelt, Wiesbaden (DE); Klaus Wirth, Kriftel (DE); Thomas Licher, Bad Soden (DE); Armin Hofmeister, Dexheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 803 days.

(21) Appl. No.: 11/680,668

(22) Filed: Mar. 1, 2007

(65) Prior Publication Data
US 2007/0225323 A1     Sep. 27, 2007

Related U.S. Application Data

(63) Continuation of application No. PCT/EP2005/009654, filed on Sep. 8, 2005.

(30) Foreign Application Priority Data

Sep. 23, 2004   (DE) ................ 10 2004 046 492

(51) Int. Cl.
  *C07D 217/00*   (2006.01)
  *A61K 31/47*   (2006.01)
(52) U.S. Cl. ........................ 514/307; 546/146
(58) Field of Classification Search ........................ None
  See application file for complete search history.

(56) References Cited

FOREIGN PATENT DOCUMENTS

| WO | WO 01/32624 | 5/2001 |
|----|-------------|--------|
| WO | WO 03/048129 | 6/2003 |
| WO | WO 03/055880 | 7/2003 |
| WO | WO 2004/085404 | 10/2004 |

*Primary Examiner*—Zinna N Davis
(74) *Attorney, Agent, or Firm*—Jiang Lin

(57) ABSTRACT

The present invention relates to substituted 4-phenyltetrahydroisoquinoline compounds of the structure of formula I

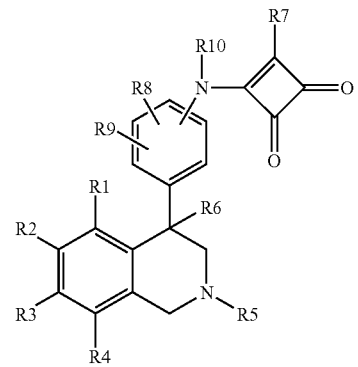

and pharmaceutical compositions comprising them wherein the R groups are herein defined. These are excellent inhibitors of the sodium-hydrogen exchanger (NHE), in particular of the sodium-hydrogen exchanger of subtype 3 (NHE3). As such these compounds are useful in the treatment of various disorders of the renal and respiratory systems such as acute or chronic renal failure, pulmonary complications, biliary function disorders, respiratory disorders such as snoring or sleep apneas and cardiovascular/central nervous system disorders such as stroke. More specifically, the present invention relates to substituted 4-phenyl-tetrahydroisoquinolines, derivatives thereof and compositions containing them formulated in combination with other compounds which also regulate the intracellular pH environment such as inhibitors of carbonic anhydrase and inhibitors of the transport systems that carry bicarbonate ions, such as of the sodium-bicarbonate co-transporter (NBC) or the sodium-dependent chloride-bicarbonate exchanger.

8 Claims, No Drawings

SUBSTITUTED 4-PHENYLTETRAHYDROISOQUINOLINES, PHARMACEUTICAL COMPOSITIONS THEREOF, METHODS FOR THEIR PREPARATION AND THERAPEUTIC USE

CROSS-REFERENCE TO RELATED APPLICATIONS

This application is a continuation of International Patent Application No. PCT/EP2005/009654 filed on Sep. 8, 2005 which is incorporated herein by reference in its' entirety which also claims the benefit of priority of German Patent Application No. 10/2004 046 492.8 filed on Sep. 23, 2004.

FIELD OF THE INVENTION

The present invention relates to compounds and compositions comprising them for the treatment of various disorders of the renal and respiratory systems such as acute or chronic renal failure, biliary function disorders, respiratory disorders such as snoring or sleep apneas and cardiovascular/central nervous system disorders such as stroke. More specifically, the present invention relates to substituted 4-phenyl-tetrahydroisoquinolines, derivatives thereof and compositions containing them. More specifically, the present invention relates to substituted 4-phenyltetrahydroisoquinoline compounds and pharmaceutical compositions comprising them which are excellent inhibitors of the sodium-hydrogen exchanger (NHE), in particular of the sodium-hydrogen exchanger of subtype 3 (NHE3).

BACKGROUND OF THE INVENTION

Compounds and pharmaceutical compositions of the present invention of this type are useful in the prevention or treatment of various disorders. For instance, the substituted 4-phenyltetrahydroisoquinoline compounds and pharmaceutical compositions comprising them which are excellent inhibitors of the sodium-hydrogen exchanger (NHE) are of surprising therapeutic value in the treatment of respiratory disorders, including snoring, as well as improvement of the respiratory drive. The NHE-3 inhibitor compounds are also useful in the treatment of acute and chronic disorders of the kidneys and of the intestines, disorders resulting from ischemic and/or reperfusion events, as well as those resulting from proliferative or fibrotic events, the treatment or prophylaxis of disorders of the central nervous system, of lipid metabolism and of diabetes, of blood coagulation and of infestation by parasites.

The NHE3 inhibitors known in the prior art hitherto are derived, for example, from compounds of the acylguanidine type (EP825178), norbornylamine types (WO0144164), 2-guanidinoquinazoline type (WO0179186), benzamidine type (WO0121582, WO0172742) or tetrahydroisoquinoline type (WO03048129, WO03055880). The squalamine which has likewise been described as an NHE3 inhibitor (M. Donowitz et al. Am. J. Physiol. 276 (Cell Physiol. 45):C136-C144), according to the current state of knowledge, does not act directly like the compounds of the formula I or II, but rather via an indirect mechanism and thus does not achieve its maximum strength of action until after one hour. Such NHE3 inhibitors having different types of mechanistic action are suitable, for example, as combination partners of the present inventive compounds.

Clonidine, which is distantly related to the inventive compounds, is known to be a weak NHE inhibitor. However, its action on the NHE3 of the rat is extremely moderate at a half-maximum inhibitory concentration ($IC_{50}$) of 620 µM. Instead, it has a certain selectivity for the NHE2 (J. Orlowski et al. J. Biol. Chem. 268, 25536). It should therefore be referred to rather as an NHE2 inhibitor. In addition to the weak NHE action, clonidine has a high affinity for the adrenergic alpha2 receptor and imidazoline I1 receptor, which causes strong blood sugar-lowering action (Ernsberger et al. Eur. J. Pharmacol. 134, 1, 1987).

Compounds which are similar to clonidine but have a thiophene instead of the phenyl ring are disclosed in DE1941761. The structures of formula I disclosed and claimed herein differ from existing compounds by the fusing of a thieno-substituent to the imidazole moiety of the formula I or II. This distinction allows the above-described clonidine-like undesired cardiovascular effects mediated by alpha-adrenoreceptor action to be eliminated. At the same time, as a consequence of the substitution differences, the NHE-inhibiting properties of the compounds described here are enhanced down to the micromolar and submicromolar range, while the compounds disclosed by DE1941761 exhibit only very weakly pronounced NHE-inhibiting effects, if any. For instance, the hypotensive compound described in the application DE1941761, tiamenidine, in a therapeutically utilizable concentration range, has no relevant inhibitory actions on any of the NHE subtypes investigated, NHE1, NHE2, NHE3 and NHE5. The application WO03053434 proposes NHE3 inhibitors of the imidazoline type, the patent application WO 03101984 of the thiophene type and the application DE10304374 of the imidazole type.

Previously disclosed NHE3 inhibitors are derived for example from compounds of the acylguanidine type (EP825178), norbornylamine type (WO0144164), 2-guanidinoquinazoline type (WO0179186) or benzamidine type (WO0121582, WO017242). Squalamine, which is likewise described as an NHE3 inhibitor (M. Donowitz et al. Am. J. Physiol. 276 (Cell Physiol. 45):C136-C144) does not according to the current state of knowledge act immediately like the compounds of the formula I, but acts via an indirect mechanism and thus reaches its maximum strength of effect only after one hour. Such NHE3 inhibitors acting via different mechanism are suitable for example as combination partners for the present compounds of the invention.

Tetrahydroisoquinolines as inhibitors of the sodium-hydrogen exchanger of subtype 3 (NHE3) have been described in the applications WO03048129 and DE10312963. The patent application WO03055880 describes the related class of tetrahydroisoquinolinium salt compounds as NHE3 inhibitors. It has now been found, surprisingly, that the compounds of the formula I described herein are likewise potent inhibitors of NHE3 and moreover have advantageous pharmacological and pharmacokinetic properties. Thus, the compounds are notable for improved properties such as, for example, a high selectivity for the sodium-hydrogen exchanger with a negligible effect on hERG potassium channels.

NHE3 is found in the body of various species preferentially in the bile, the intestine and the kidney (Larry Fliegel et al., Biochem. Cell. Biol. 76:735-741, 1998), but has also been detected in the brain (E. Ma et al., Neuroscience 79:591-603).

On the basis of the NHE-inhibitory properties, the 4-phenyltetrahydroisoquinoline compounds of the present invention as defined by formula I herein and their pharmaceutically acceptable salts are suitable for the prevention and treatment of diseases which are caused by activation or by an activated NHE, and of diseases which are caused secondarily by the NHE-related damage.

Optionally, the NHE inhibitors described herein can be combined with other compounds which also regulate the intracellular pH environment Suitable combination comprise the formulation with other inhibitors of the enzyme group of carbonic anhydrases and inhibitors of the transport systems that carry bicarbonate ions, such as of the sodium-bicarbonate co-transporter (NBC) or of the sodium-dependent chloride-bicarbonate exchanger, and with other NHE inhibitors with an inhibitory effect on other NHE subtypes, because the pharmacologically relevant pH-regulating effects of the NHE inhibitors described herein can be enhanced or modulated thereby.

The use of compounds of the present invention relates to the prevention and the treatment of acute and chronic diseases in veterinary and human medicine.

The pharmacological effect of the compounds of the formula I is characterized in that they lead to an improvement in the respiratory drive. They can therefore be used for the treatment of impaired respiratory In the present invention, it has surprisingly been possible to show that the compounds of formula I, below, constitute potent inhibitors of sodium/proton exchange (NHE), especially of sub-type 3 sodium/proton exchanger (NHE3).

SUMMARY OF THE INVENTION

The present invention relates to substituted 4-phenyltetrahydroisoquinoline compounds and pharmaceutical compositions comprising them which are excellent inhibitors of the sodium-hydrogen exchanger (NHE), in particular of the sodium-hydrogen exchanger of subtype 3 (NHE3). As such these compounds are useful in the treatment of various disorders of the renal and respiratory systems such as acute or chronic renal failure, pulmonary complications, biliary function disorders, respiratory disorders such as snoring or sleep apneas and cardiovascular/central nervous system disorders such as stroke. More specifically, the present invention relates to substituted 4-phenyltetrahydroisoquinolines, derivatives thereof and compositions containing them formulated in combination with other compounds which also regulate the intracellular pH environment such as inhibitors of carbonic anhydrase and inhibitors of the transport systems that carry bicarbonate ions, such as of the sodium-bicarbonate co-transporter (NBC) or the sodium-dependent chloride-bicarbonate exchanger

DETAILED DESCRIPTION OF THE INVENTION

The invention relates to potent inhibitors of sodium/proton exchange (NHE), especially of subtype 3 sodium/proton exchanger (NHE3).

Structurally, the compounds are represented by those compounds of formula I

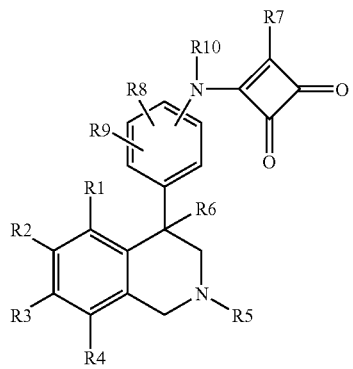

wherein:
R1, R2, R3 and R4 are independently selected from the group consisting of hydrogen, F, Cl, Br, I, CN, $NO_2$ and R11-$(C_mH_{2m})$-$A_n$-, wherein;
m is zero, 1, 2, 3 or 4;
n is zero or 1;
R11 is selected from the group consisting of hydrogen, methyl, $C_pF_{2p+1}$ and phenyl;
P is 1, 2 or 3;
A is oxygen, NH, $N(CH_3)$ or $S(O)_q$;
q is zero, 1 or 2;
R5 is hydrogen, an alkyl having 1, 2, 3, 4, 5 or 6 C atoms which may be partly or completely fluorinated, or a cycloalkyl having 3, 4, 5 or 6 C atoms;
R6 is selected from the group consisting of hydrogen, OH, F, $CF_3$, methyl, ethyl, isopropyl and cyclopropyl;
R7 is hydrogen, alkyl having 1, 2, 3, 4, 5 or 6 C atoms, cycloalkyl having 3, 4, 5 or 6 C atoms, OR12 or NR13R14;
R12 is hydrogen, alkyl having 1, 2, 3, 4, 5 or 6 C atoms which may be partly or completely fluorinated, or cycloalkyl having 3, 4, 5 or 6 C atoms;
R13 and R14 are independently selected from the group consisting of hydrogen, cycloalkyl having 3, 4, 5 or 6 C atoms; alkyl having 1, 2, 3, 4, 5 or 6 C atoms which may be partly or completely fluorinated, phenyl, phenylalkyl having 1, 2 or 3 C atoms in the alkyl moiety, heteroaryl or heteroarylmethyl, wherein the phenyl and heteroaryl substituents are un-substituted or substituted by 1, 2, 3, 4 or 5 substituents selected from the group consisting of fluorine, chlorine, methyl, $CF_3$, methoxy and OH;
and where the alkyl substituents are unsubstituted or are substituted by 1, 2 or 3 substituents selected from the group consisting of an alkoxy having 1, 2, 3 or 4 C atoms, NR15R16 and cycloalkyl having 3, 4, 5 or 6 C atoms;
R15 and R16 are selected from the group consisting of hydrogen and alkyl having 1, 2, 3 or 4 C atoms; or
R13 and R14 together with the N atom via which they are connected comprise a 3, 4, 5, 6, 7, 8 or 9-membered ring, where one C atom of the ring may be optionally replaced by an oxygen atom or an $NCH_3$ group,
R8 and R9 are independently selected from the group consisting of one another hydrogen, F, Cl, OH, $CH_3$, $CH_3O$, $CF_3$, $CF_3CH_2O$ and $CH_3SO_2$;
R10 is hydrogen, methyl or ethyl;

and a pharmaceutically acceptable salt and trifluoroacetate thereof.

Preferably, compounds of the present invention comprise those of the formula I wherein:

R1, R2, R3 and R4 are independently selected from the group consisting of hydrogen, F, Cl, Br, CN or R11-$(C_mH_{2m})$-$A_n$- wherein:

m is zero or 1;
n is zero or 1;
R11 is hydrogen, methyl, $C_pF_{2p+1}$— or phenyl;
P is 1 or 2;
A is oxygen or $S(O)_q$;
q is zero, 1 or 2;
R5 is hydrogen, methyl, ethyl or cyclopropyl;
R6 is hydrogen or methyl;
R7 is OR12 or NR13R14;
R12 is a hydrogen or alkyl having 1, 2 or 3 C atoms;
R13 and R14 are independently selected from the group consisting of hydrogen, an alkyl having 1, 2, 3, 4, 5 or 6 C atoms which may be partly or completely fluorinated, cycloalkyl having 3, 4, 5 or 6 C atoms, phenyl, phenylalkyl having 1, 2 or 3 C atoms in the alkyl moiety, heteroaryl or heteroarylmethyl; where the phenyl and heteroaryl substituents are un-substituted or are substituted by 1, 2, 3, 4 or 5 substituents selected from the group consisting of fluorine, chlorine, methyl, $CF_3$, methoxy and OH wherein the alkyl chains are substituted or un-substituted by 1, 2 or 3 groups selected from the group of alkoxy having 1, 2, 3 or 4 C atoms, NR15R16 and cycloalkyl having 3, 4, 5 or 6 C atoms;
R15 and R16 are independently selected from the group consisting of hydrogen or alkyl having 1, 2, 3 or 4 C atoms; or
R13 and R14 together with the N atom with which they are connected comprise a 3, 4, 5, 6, 7 or 8-membered ring, where one C atom of the ring may be replaced by an oxygen atom or an $NCH_3$ group;
R8 and R9 are independently selected from the group consisting of hydrogen, F, Cl and $CH_3$;
R10 is hydrogen or methyl; and, a pharmaceutically acceptable salt and trifluoroacetate thereof.

More particularly, the present invention comprises compounds of formula I wherein:
R1 and R3 are hydrogen;
R2 and R4 are independently of one another hydrogen or Cl;
R5 is hydrogen, methyl or ethyl;
R6 is hydrogen or methyl;
R7 is OR12 or NR13R14;
R12 is hydrogen or alkyl having 1, 2 or 3 C atoms;
R13 and R14 are selected from the group consisting of hydrogen, an alkyl having 1, 2, 3, 4, 5 or 6 C atoms which may be partly or completely fluorinated, cycloalkyl having 3, 4, 5 or 6 C atoms, phenyl, phenylalkyl having 1, 2 or 3 C atoms in the alkyl moiety, heteroaryl or heteroarylmethyl; where the phenyl and heteroaryl substituents are substituted or un-substituted or are by 1, 2, 3, 4 or 5 substituents selected from the group consisting of fluorine, chlorine, methyl, $CF_3$, methoxy and OH; wherein the alkyl groups are substituted or un-substituted or 1, 2 or 3 substituents are selected from the group of alkoxy having 1, 2, 3 or 4 C atoms, NR15R16 and cycloalkyl having 3, 4, 5 or 6 C atoms;
R15 and R16 are independently selected from the group consisting of hydrogen or an alkyl having 1, 2, 3 or 4 C atoms; or;
R13 and R14 are together with the N atom via which they are connected together a 3, 4, 5, 6, 7 or 8-membered ring, where one C atom of the ring may be replaced by an oxygen atom or an $NCH_3$ group;
R8 and R9 are independently selected from the group consisting of one another hydrogen, F, Cl or $CH_3$;
R10 hydrogen or methyl;

and a pharmaceutically acceptable salt and trifluoroacetate thereof.

One embodiment relates to compounds of the formula I in which R1 is hydrogen, F, Cl, Br, CN or R11-$(C_mH_{2m})$-$A_n$-, where m is zero or 1, n is zero or 1, R11 is hydrogen, methyl, $C_pF_{2p+1}$— or phenyl, where p is 1 or 2, and A is oxygen or $S(O)_q$, where q is zero, 1 or 2; compounds of the formula I in which R1 is hydrogen are preferred.

Another embodiment relates to compounds of the formula I in which R2 is hydrogen, F, Cl, Br, CN or R11-$(C_mH_{2m})$-$A_n$-, where m is zero or 1, n is zero or 1, R11 is hydrogen, methyl, $C_pF_{2p+1}$— or phenyl, where p is 1 or 2, and A is oxygen or $S(O)_q$, where q is zero, 1 or 2; compounds of the formula I in which R2 is hydrogen or Cl, in particular Cl, are preferred.

A third embodiment relates to compounds of the formula I in which R3 is hydrogen, F, Cl, Br, CN or R 1-$(C_mH_{2m})$-$A_n$-, where m is zero or 1, n is zero or 1, R11 is hydrogen, methyl, $C_pF_{2p+1}$— or phenyl, where p is 1 or 2, and A is oxygen or $S(O)_q$, where q is zero, 1 or 2; compounds of the formula I in which R3 is hydrogen are preferred.

Another embodiment relates to compounds of the formula I in which R4 is hydrogen, F, Cl, Br, CN or R11-$(C_mH_{2m})$-$A_n$-, where m is zero or 1, n is zero or 1, R11 is hydrogen, methyl, $C_pF_{2p+1}$— or phenyl, where p is 1 or 2, and A is oxygen or $S(O)_q$, where q is zero, 1 or 2; compounds of the formula I in which R4 is hydrogen or Cl, in particular Cl, are preferred.

A further embodiment relates to compounds of the formula I in which R5 is hydrogen, methyl, ethyl or cyclopropyl, preferably hydrogen, methyl or ethyl.

A further embodiment relates to compounds of the formula I in which R6 is hydrogen or methyl.

A further embodiment relates to compounds of the formula I in which R7 is OR12 or NR13R14, where R12 is hydrogen or alkyl having 1, 2 or 3 C atoms and where R13 and R14 are independently of one another hydrogen, alkyl having 1, 2, 3, 4, 5 or 6 C atoms which may be partly or completely fluorinated, cycloalkyl having 3, 4, 5 or 6 C atoms, phenyl, phenylalkyl having 1, 2 or 3 C atoms in the alkyl moiety, heteroaryl or heteroarylmethyl, where the phenyl and heteroaryl substituents are unsubstituted or substituted by 1, 2, 3, 4 or 5 substituents selected from the group consisting of fluorine, chlorine, methyl, $CF_3$, methoxy and OH and where the alkyl substituents are unsubstituted or are substituted by 1, 2 or 3 substituents selected from the group of alkoxy having 1, 2, 3 or 4 C atoms, in particular methoxy, NR15R16, where R15 and R16 are independently of one another hydrogen or alkyl having 1, 2, 3 or 4 C atoms, in particular methyl, and cycloalkyl having 3, 4, 5 or 6 C atoms, in particular cyclopropyl, or where R13 and R14 together with the N atom via which they are connected together form a 3, 4, 5, 6, 7 or 8-membered ring, where one C atom of the ring may be replaced by an oxygen atom or an $NCH_3$ group, for example R13 and R14 form together with the N atom via which they are connected together a saturated ring such as pyrrolidino, piperidino, perhydroazepino, morpholino, 4-methylpiperazino, in particular pyrrolidino.

A further embodiment relates to compounds of the formula I in which R8 is hydrogen, F, Cl or methyl.

A further embodiment relates to compounds of the formula I in which R9 is hydrogen, F, Cl or methyl.

A further embodiment relates to compounds of the formula I in which R10 is hydrogen or methyl.

Specific preference is given to compounds of the formula I selected from the group:

6,8-dichloro-2-methyl-4-[4N-(2-ethoxy-3,4-dioxocyclobuten-1-yl)amino]phenyl-1,2,3,4-tetrahydroisoquinoline,
6,8-dichloro-2-methyl-4-[3N-(2-ethoxy-3,4-dioxocyclobuten-1-yl)amino]phenyl-1,2,3,4-tetrahydroisoquinoline,
6,8-dichloro-2-methyl-4-[2N-(2-ethoxy-3,4-dioxocyclobuten-1-yl)amino]phenyl-1,2,3,4-tetrahydroisoquinoline,
6,8-dichloro-2-methyl-4(S)-[4N-(2-ethoxy-3,4-dioxocyclobuten-1-yl)amino]phenyl-1,2,3,4-tetrahydroisoquinoline,
6,8-dichloro-2-methyl-4(S)-[3N-(2-ethoxy-3,4-dioxocyclobuten-1-yl)amino]phenyl-1,2,3,4-tetrahydroisoquinoline,
6,8-dichloro-2-methyl-4(R)-[2N-(2-ethoxy-3,4-dioxocyclobuten-1-yl)amino]phenyl-1,2,3,4-tetrahydroisoquinoline,
6,8-dichloro-2-methyl-4-[4N-(2-hydroxy-3,4-dioxocyclobuten-1-yl)amino]phenyl-1,2,3,4-tetrahydroisoquinoline,
6,8-dichloro-2-methyl-4-[3N-(2-hydroxy-3,4-dioxocyclobuten-1-yl)amino]phenyl-1,2,3,4-tetrahydroisoquinoline,
6,8-dichloro-2-methyl-4-[2N-(2-hydroxy-3,4-dioxocyclobuten-1-yl)amino]phenyl-1,2,3,4-tetrahydroisoquinoline,
6,8-dichloro-2-methyl-4-[4N-(2-amino-3,4-dioxocyclobuten-1-yl)amino]phenyl-1,2,3,4-tetrahydroisoquinoline,
6,8-dichloro-2-methyl-4-[3N-(2-amino-3,4-dioxocyclobuten-1-yl)amino]phenyl-1,2,3,4-tetrahydroisoquinoline,
6,8-dichloro-2-methyl-4-[2N-(2-amino-3,4-dioxocyclobuten-1-yl)amino]phenyl-1,2,3,4-tetrahydroisoquinoline,
6,8-dichloro-2-methyl-4(S)-[4N-(2-amino-3,4-dioxocyclobuten-1-yl)amino]phenyl-1,2,3,4-tetrahydroisoquinoline,
6,8-dichloro-2-methyl-4(S)-[3N-(2-amino-3,4-dioxocyclobuten-1-yl)amino]phenyl-1,2,3,4-tetrahydroisoquinoline,
6,8-dichloro-2-methyl-4(S)-[2N-(2-amino-3,4-dioxocyclobuten-1-yl)amino]phenyl-1,2,3,4-tetrahydroisoquinoline,
6,8-dichloro-2-methyl-4-[4N-(2-N-cyclohexyl-N-methylamino-3,4-dioxocyclobuten-1-yl)amino]phenyl-1,2,3,4-tetrahydroisoquinoline,
6,8-dichloro-2-methyl-4-[4N-(2-dimethylamino-3,4-dioxocyclobuten-1-yl)amino]phenyl-1,2,3,4-tetrahydroisoquinoline,
6,8-dichloro-2-methyl-4-[3N-(2-dimethylamino-3,4-dioxocyclobuten-1-yl)amino]phenyl-1,2,3,4-tetrahydroisoquinoline,
6,8-dichloro-2-methyl-4(S)-[4N-(2-dimethylamino-3,4-dioxocyclobuten-1-yl)amino]phenyl-1,2,3,4-tetrahydroisoquinoline,
6,8-dichloro-2-methyl-4(R)-[2N-(2-dimethylamino-3,4-dioxocyclobuten-1-yl)amino]phenyl-1,2,3,4-tetrahydroisoquinoline,
6,8-dichloro-2-methyl-4(S)-[3N-(2-dimethylamino-3,4-dioxocyclobuten-1-yl)amino]phenyl-1,2,3,4-tetrahydroisoquinoline,
6,8-dichloro-2-methyl-4(S)-[4N-(2-N-(1-butyl)-N-methylamino-3,4-dioxocyclobuten-1-yl)amino]phenyl-1,2,3,4-tetrahydroisoquinoline,
6,8-dichloro-2-methyl-4-[4N-(2-dipropylamino-3,4-dioxocyclobuten-1-yl)amino]phenyl-1,2,3,4-tetrahydroisoquinoline,
6,8-dichloro-2-methyl-4-[4N-(2-(N-isobutyl-N-methylamino)-3,4-dioxocyclobuten-1-yl)amino]phenyl-1,2,3,4-tetrahydroisoquinoline,
6,8-dichloro-2-methyl-4-[4N-(2-(N-methoxyethyl)-N-methylamino)-3,4-dioxocyclobuten-1-yl)amino]phenyl-1,2,3,4-tetrahydroisoquinoline,
6,8-dichloro-2-methyl-4(S)-[4N-(2-diethylamino-3,4-dioxocyclobuten-1-yl)amino]phenyl-1,2,3,4-tetrahydroisoquinoline,
6,8-dichloro-2-methyl-4(S)-[4N-(2-(N-isopropyl-N-methylamino)-3,4-dioxocyclobuten-1-yl)amino]phenyl-1,2,3,4-tetrahydroisoquinoline,
6,8-dichloro-2-methyl-4-[N-(2-(N-cyclopropyl methyl-N-propylamino)-3,4-dioxocyclobuten-1-yl)amino]phenyl-1,2,3,4-tetrahydroisoquinoline,
6,8-dichloro-2-methyl-4(S)-[3N-(2-diethylamino-3,4-dioxocyclobuten-1-yl)amino]phenyl-1,2,3,4-tetrahydroisoquinoline,
6,8-dichloro-2-methyl-4(S)-[3N-(2-N-methyl-N-isopropyl)amino-3,4-dioxocyclobuten-1-yl)amino]phenyl-1,2,3,4-tetrahydroisoquinoline,
6,8-dichloro-2-methyl-4(S)-[4N-(2N-ethyl-N-isopropyl)amino-3,4-dioxocyclobuten-1-yl)amino]phenyl-1,2,3,4-tetrahydroisoquinoline,
6,8-dichloro-2-methyl-4(S)-[3N-(2-N-methyl-N-propyl)amino-3,4-dioxocyclobuten-1-yl)amino]phenyl-1,2,3,4-tetrahydroisoquinoline,
6,8-dichloro-2-methyl-4(S)-[3N-(2-N-pyrrolidino-3,4-dioxocyclobuten-1-yl)amino]phenyl-1,2,3,4-tetrahydroisoquinoline,
6,8-dichloro-2-methyl-4(S)-[4N-(2-N-cyclopropylamino)-3,4-dioxocyclobuten-1-yl)amino]phenyl-1,2,3,4-tetrahydroisoquinoline,
6,8-dichloro-2-methyl-4(S)-[4N-(2-N-pyrrolidino-3,4-dioxocyclobuten-1-yl)amino]phenyl-1,2,3,4-tetrahydroisoquinoline,
6,8-dichloro-2-methyl-4(R)-[2N-(2-N-methyl-N-propylamino)-3,4-dioxocyclobuten-1-yl)amino]phenyl-1,2,3,4-tetrahydroisoquinoline,
6,8-dichloro-2-methyl-4-[4N-(2-N-benzyl-N-methylamino)-3,4-dioxocyclobuten-1-yl)amino]phenyl-1,2,3,4-tetrahydroisoquinoline,
6,8-dichloro-2-methyl-4(R)-[2N-(2-diethylamino-3,4-dioxocyclobuten-1-yl)amino]phenyl-1,2,3,4-tetrahydroisoquinoline,
6,8-dichloro-2-methyl-4(R)-[2N-(2-dipropylamino)-3,4-dioxocyclobuten-1-yl)amino]phenyl-1,2,3,4-tetrahydroisoquinoline,
6,8-dichloro-2-methyl-4(R)-[2N-(2-N-pyrrolidino-3,4-dioxocyclobuten-1-yl)amino]phenyl-1,2,3,4-tetrahydroisoquinoline,
6,8-dichloro-2-methyl-4(R)-[2N-(2-N-methyl-N-isopropyl)amino-3,4-dioxocyclobuten-1-yl)amino]phenyl-1,2,3,4-tetrahydroisoquinoline,
6,8-dichloro-2-methyl-4-[4N-(2-N-phenylamino-3,4-dioxocyclobuten-1-yl)amino]phenyl-1,2,3,4-tetrahydroisoquinoline,
6,8-dichloro-2-methyl-4-[2N-(2-N-methylamino-3,4-dioxocyclobuten-1-yl)amino]phenyl-1,2,3,4-tetrahydroisoquinoline, 6,8-dichloro-2-methyl-4-[2N-(2-N-(1-hexylamino)-3,4-dioxocyclobuten-1-yl)amino]phenyl-1,2,3,4-tetrahydroisoquinoline, 6,8-dichloro-2-methyl-4-[2N-(2-N-isopropylamino-3,4-dioxocyclobuten-1-yl)amino]phenyl-1,2,3,4-tetrahydroisoquinoline, 6,8-dichloro-2-methyl-4-[2N-(2-N-cyclopentylamino-3,4-dioxocyclobuten-1-yl)amino]phenyl-1,2,3,4-tetrahydroisoquinoline, 6,8-dichloro-2-methyl-4-[2N-(2N-(2-furylmethyl)amino-3,4-dioxocyclobuten-1-yl)amino]phenyl-1,2,3,4-tetrahydroisoquinoline, 6,8-dichloro-2-methyl-4-[2N-(2-N-ethylamino-3,4-dioxocyclobuten-1-yl)amino]phenyl-1,2,3,4-tetrahydroisoquinoline, 6,8-dichloro-2-methyl-4-[2N-(2-N-dimethylaminoethylamino-3,4-dioxocyclobuten-1-yl)amino]phenyl-1,2,3,4-tetrahydroisoquinoline, 6,8-dichloro-2-methyl-4-[4N-(2-N-ethylamino-3,4-dioxocyclobuten-1-yl)amino]phenyl-1,2,3,4-tetrahydroisoquinoline, 6,8-dichloro-2-methyl-4-[2N-(2N-(3-picolylmethyl)amino-3,4-dioxocyclobuten-1-yl)amino]phenyl-1,2,3,4-tetrahydroisoquinoline, 6,8-dichloro-2-methyl-4-[4N-(2N-methylamino-3,4-dioxocyclobuten-1-yl)amino]phenyl-1,2,3,4-tetrahydroisoquinoline, 6,8-dichloro-2-methyl-4-[4N-(2N-cyclopropylamino-3,4-dioxocyclobuten-1-yl)amino]phenyl-1,2,3,4-tetrahydroisoquinoline, 6,8-dichloro-2-methyl-4-[4N-(2N-isopropylamino-3,4-dioxocyclobuten-1-yl)amino]phenyl-1,2,3,4-tetrahydroisoquinoline, 6,8-dichloro-2-methyl-4-[4N-(2N-(2-furylmethyl)amino-3,4-dioxocyclobuten-1-yl)amino]phenyl-1,2,3,4-tetrahydroisoquinoline, 6,8-dichloro-2-methyl-4-[4N-(2N-dimethylaminoethylamino)-3,4-dioxocyclobuten-1-yl)amino]phenyl-1,2,3,4-tetrahydroisoquinoline, 6,8-dichloro-2-methyl-4-[4N-(1-hexylamino)-3,4-dioxocyclobuten-1-yl)amino]phenyl-1,2,3,4-tetrahydroisoquinoline, 6,8-dichloro-2-methyl-4-[4N-(2-picolylamino)-3,4-dioxocyclobuten-1-yl)amino]phenyl-1,2,3,4-tetrahydroisoquinoline, 6,8-dichloro-2-methyl-4-[4N-2-methylamino-3,4-dioxocyclobuten-1-yl)amino]phenyl-1,2,3,4-tetrahydroisoquinoline, 6,8-dichloro-2-methyl-4-[4N-(2-ethylamino)-3,4-dioxocyclobuten-1-yl)amino]phenyl-1,2,3,4-tetrahydroisoquinoline, 6,8-dichloro-2-methyl-4-[3N-(2-(2-furylmethylamino)-3,4-dioxocyclobuten-1-yl)amino]phenyl-1,2,3,4-tetrahydroisoquinoline, 6,8-dichloro-2-methyl-4-[3N-(2-cyclopentylamino-3,4-dioxocyclobuten-1-yl)amino]phenyl-1,2,3,4-tetrahydroisoquinoline, 6,8-dichloro-2-methyl-4-[3N-(2-isopropylamino)-3,4-dioxocyclobuten-1-yl)amino]phenyl-1,2,3,4-tetrahydroisoquinoline, 6,8-dichloro-2-methyl-4-[3N-(2N-dimethylaminoethylamino)-3,4-dioxocyclobuten-1-yl)amino]phenyl-1,2,3,4-tetrahydroisoquinoline, 6,8-dichloro-2-methyl-4(R)-[2N-(2-isopropylamino-3,4-dioxocyclobuten-1-yl)amino]phenyl-1,2,3,4-tetrahydroisoquinoline, 6,8-dichloro-2-methyl-4(R)-[3N-(2-methylamino-3,4-dioxocyclobuten-1-yl)amino]phenyl-1,2,3,4-tetrahydroisoquinoline, and 6,8-dichloro-2-methyl-4(R)-[2N-(2-methylamino-3,4-dioxocyclobuten-1-yl)amino]phenyl-1,2,3,4-tetrahydroisoquinoline and a pharmaceutically acceptable salt and/or trifluoroacetate thereof.

If the compounds of the formula I comprise one or more centers of asymmetry, these may independently of one another have either the S or the R configuration. The compounds may be in the form of optical isomers, of enantiomers, of diastereomers, of racemates or of mixtures in all ratios thereof.

The present invention includes all tautomeric forms of the compounds of the formula I.

Alkyl chains may be straight-chain or branched. This also applies when they have substituents or occur as substituents of other alkyl chains, for example in fluoroalkyl- or alkoxy substituents. Examples of alkyl groups are methyl, ethyl, n-propyl, isopropyl (=1-methylethyl), n-butyl, isobutyl (=2-methylpropyl), sec-butyl (=1-methylpropyl), tert-butyl (=1,1-dimethyl-ethyl), n-pentyl, isopentyl, tert-pentyl, neopentyl or hexyl. Preferred alkyl substituents are methyl, ethyl, n-propyl, isopropyl, n-butyl, tert-butyl, n-pentyl, n-hexyl. One or more, for example 1, 2, 3, 4, 5, 6, 7, 8, 9, 10, 11, 12 or 13, hydrogen atoms in the alkyl groups may be replaced by fluorine atoms. Example of such fluoroalkyl substituents are trifluoromethyl, 2,2,2-trifluoroethyl, pentafluoroethyl and heptafluoroisopropyl.

Examples of cycloalkyl chains are cyclo-propyl, cyclobutyl, cyclopentyl, cyclohexyl, cycloheptyl or cyclooctyl. One or more $CH_2$ groups in the cycloalkyl chains may be replaced by O, NH or N-alkyl, for example $NCH_3$.

Phenyl groups may be substituted or un-substituted one or more times, for example once, twice or three times, by identical or different substituents. This applies likewise to substituted phenyl moieties in groups such as phenylalkyl. Examples of phenylalkyl substituents are benzyl, 1-phenylethyl or 2-phenylethyl. The moiety in mono-substituted phenyl groups may be in position 2, position 3 or position 4. Di-substituted phenyl may be substituted in position 2,3, position 2,4, position 2,5, position 2,6, position 3,4 or position 3,5. The substituents in tri-substituted phenyl groups may be in position 2,3,4, position 2,3,5, position 2,4,5, position 2,4,6, position 2,3,6 or position 3,4,5.

Heteroaryl substituents are aromatic ring compounds in which one or more ring atoms are oxygen atoms, sulfur atoms or nitrogen atoms, e.g. 1, 2, 3 or 4 nitrogen atoms, 1 or 2 oxygen atoms, 1 or 2 sulfur atoms or a combination of various heteroatoms. The heteroaryl substituents may be attached via all positions, for example via position 1, position 2, position 3, position 4, position 5, position 6, position 7 or position 8. Heteroaryl substituents may be un-substituted or substituted one or more times, for example once, twice or three times, by identical or different substituents. This likewise applies to substituted heteroaryl substituents in groups such as heteroarylmethyl. Examples of heteroaryl are 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or 5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or 5-yl, 1,2,4-oxadiazol-3- or 5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or 5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also included are the corresponding N-oxides of these compounds, for example 1-oxy-2-, -3- or -4-pyridyl. Preference is given in this connection to the 5- or 6-membered heterocycles, for example imidazolyl, pyrazolyl, pyrrolyl, triazolyl, tetrazolyl, thiazolyl, thienyl, furyl, oxazolyl and pyridyl.

If the compounds of the formula I comprise one or more acidic or basic groups or one or more basic heterocycles, the corresponding physiologically or toxicologically acceptable salts also belong to the invention, especially the pharmaceutically utilizable salts. Thus, the compounds of the formula I may be de-protonated on an acidic group and be used for example as alkali metal salts, preferably sodium or potassium salts, or as ammonium salts, for example as salts with ammonia or organic amines or amino acids. Compounds of the formula I comprising a basic group can also be used in the form of their physiologically tolerated acid addition salts with inorganic or organic acids, for example as hydrochlorides, phosphates, sulfates, methanesulfonates, acetates, lactates, maleates, fumarates, malates, gluconates etc.

The invention also relates to the method described below for preparing the compounds of the formula I.

The compounds of the formula I described herein can be prepared starting from the aniline derivatives of the formula II. For this purpose, compounds of the formula II are reacted with squaric acid derivatives of the formula III

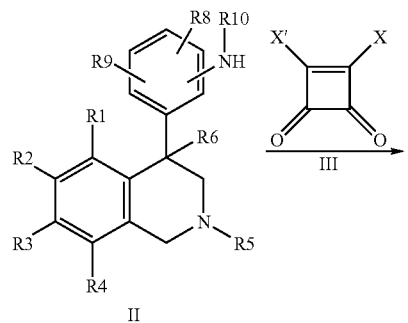

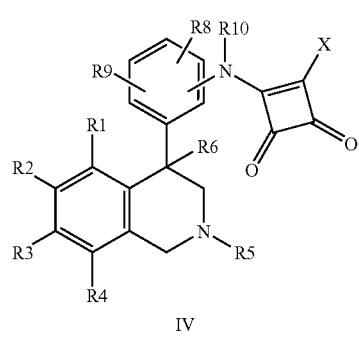

where the substituents R1, R2, R3, R4, R5, R6, R8, R9 and R10 are as defined above, X is a group which can readily undergo nucleophilic substitution, such as chlorine or phenoxy, or is defined as R7, and X' is a group which can undergo nucleophilic substitution, for example chlorine, phenoxy or alkoxy, for example ethoxy.

The compounds of the formula IV correspond to compounds of the formula I when the substituent X has the meaning of R7.

The squaric acid derivatives of the formula III can be purchased or prepared by methods known from the literature.

The compounds of the formula IV can additionally be converted in diverse manners by nucleophilic exchange with compounds of the formula V by methods known to the skilled worker into compounds of the invention of the formula I

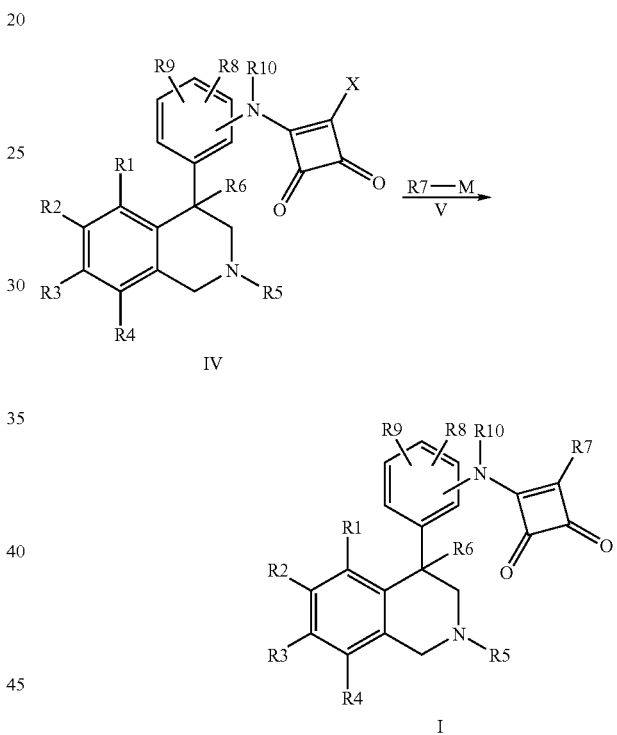

where R1, R2, R3, R4, R5, R6, R7, R8, R9, R10 and have the abovementioned meaning, X is a group which can undergo nucleophilic substitution, for example chlorine, phenoxy or alkoxy, for example ethoxy, and M is either hydrogen or a metal, in particular an alkali metal or an alkaline earth metal equivalent, for example lithium or Grignard compounds.

The compounds of the formula V can be purchased or can be prepared by methods known from the literature.

Tetrahydroisoquinolines of the formula II in which R6 is hydrogen (tetrahydroisoquinolines of the formula IIa) can be prepared for example by reduction of the carbonyl group in compounds of the formula VI and subsequent acid-catalyzed cyclization of the corresponding alcohols of the formula VII (cf. Tetrahedron Lett., 1989, 30, 5837; Org. Prep. Proced. Int., 1995, 27, 513) by known methods,

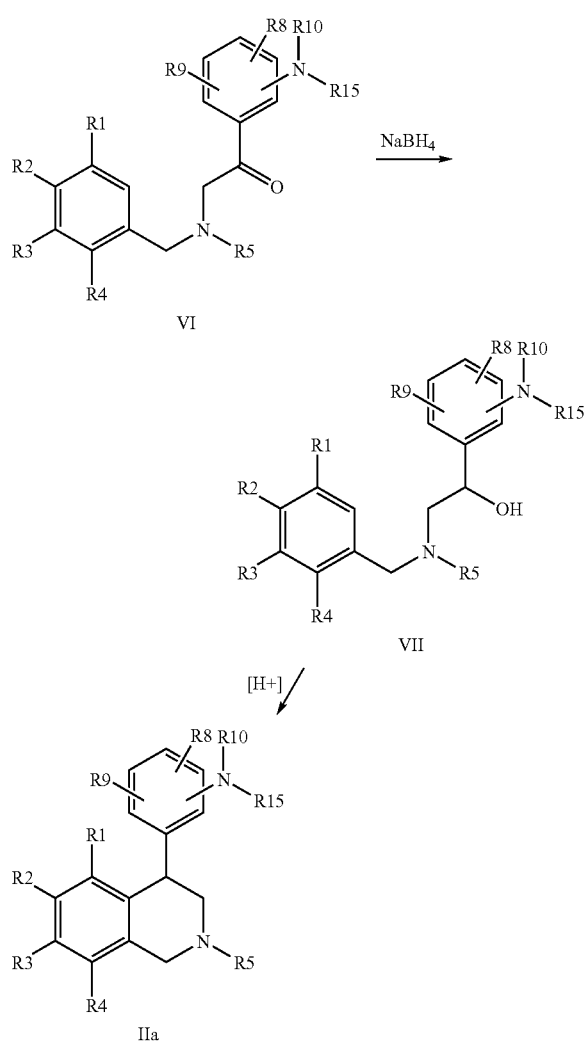

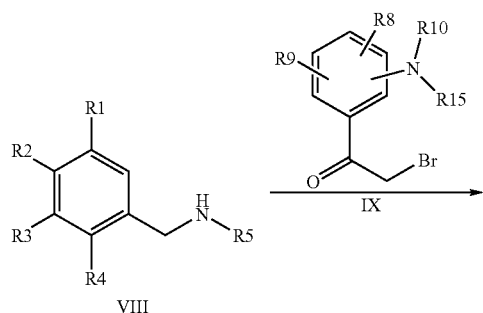

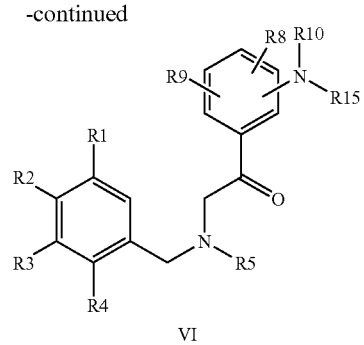

where the substituents R1, R2, R3, R4, R5, R8, R9 and R10 have the abovementioned meaning, and R15 is hydrogen or a nitrogen protective group well known by those skilled in the art, for example an acetyl substituent.

The compounds of the formula VI used above can be prepared in a manner known to those skilled in the art by alkylation of the benzylamines of the formula VIII with the appropriately substituted alpha-bromoacetophenone compounds IX wherein the substituents R1, R2, R3, R4, R5, R8, R9, R10 and R15 have the abovementioned meaning.

The alpha-bromoacetophenone compounds of the formula IX can be obtained in methods known from the literature from the corresponding acetophenone precursors by bromination as described for example in Jerry March, Advanced Organic Chemistry, Reactions, Mechanisms, and Structure. Second Edition, 7th printing, McGraw-Hill Book Company Japan, Ltd 1983, pages 537-539, Chapter: "Halogenation of Aldehydes and Ketones".

The benzylamine precursors of the formula VIII can, if not purchasable, be synthesized by standard methods known to the skilled worker for example from the corresponding benzyl chlorides or bromides of the formula X and the appropriate amine

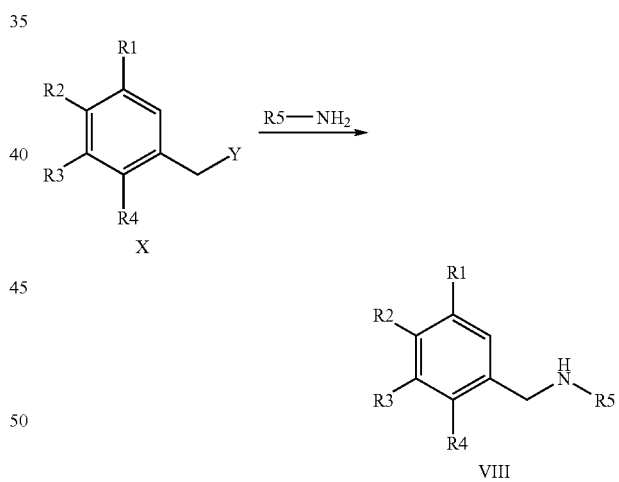

where R1, R2, R3, R4 and R5 are as defined above, and Y is a halogen, for example Cl or Br.

Branched compounds of the formula II in which R6 is not hydrogen (compounds of the formula IIb) can be prepared for example by alkylating the corresponding diphenylacetic esters of the formula XI in the alpha position with R6 by known methods. The resulting compounds of the formula XII can be converted by standard methods into the corresponding amides of the formula XIII, which can be converted in a Pictet-Spengler-analogous reaction into the desired tetrahydroisoquinolines IIb (cf. Tetrahedron; 1987, 43, 439; Chem. Pharm. Bull.; 1985, 33, 340),

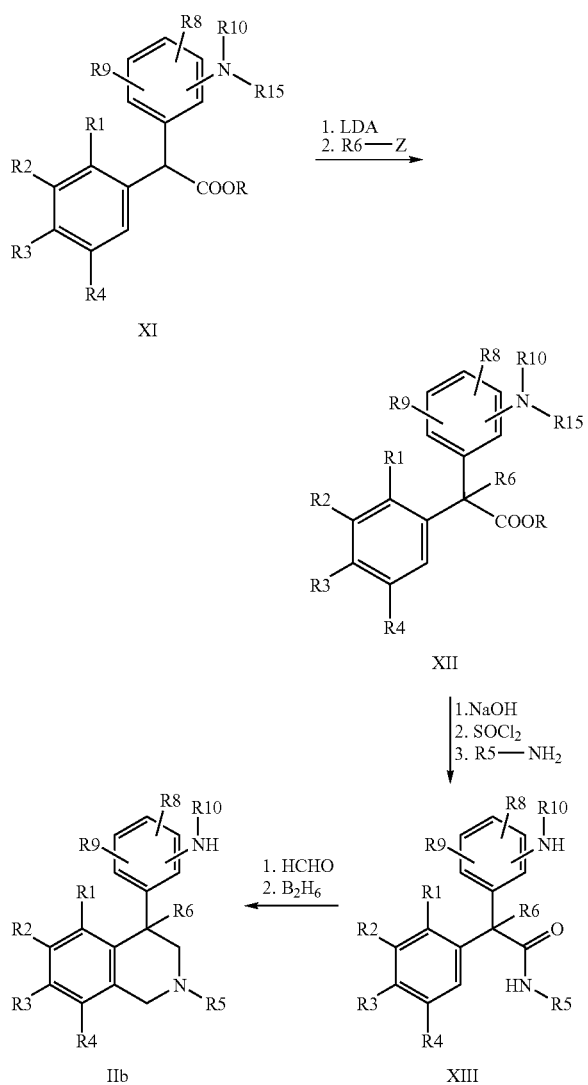

where the substituents R1, R2, R3, R4, R5, R6, R7, R8, R9, R10 and R15 have the abovementioned meanings, and where Z is a halogen, for example Cl, Br or I, and R is an alkyl having 1, 2, 3 or 4 C atoms, for example methyl or ethyl.

The compounds R5-NH$_2$ and R6-Z can be purchased or be prepared by methods known in the literature.

The compounds of formula XI are commercially available or may be obtained synthetically from a corresponding benzyl cyamide, which is phenylated in the alpha-position under a basic two-phase catalysis with a nitro-substituted fluoro- or chlorobenzene; the resulting alpha-phenylbenzyl cyamide can be hydrolyzed with base or preferably in an acidic medium to the corresponding carboxylic acid XI.

The products and/or intermediates are prepared and purified by the usual methods known in the art such as by extraction, chromatography or crystallization and drying.

It has been possible to show that compounds of the formula I are excellent inhibitors of the sodium-hydrogen exchanger (NHE), in particular of the sodium-hydrogen exchanger of subtype 3 (NHE3).

Previously disclosed NHE3 inhibitors are derived for example from compounds of the acylguanidine type (EP825178), norbornylamine type (WO0144164), 2-guanidinoquinazoline type (WO0179186) or benzamidine type (WO0121582, WO017242). Squalamine, which is likewise described as an NHE3 inhibitor (M. Donowitz et al. Am. J. Physiol. 276 (Cell Physiol. 45):C136-C144) does not according to the current state of knowledge act immediately like the compounds of the formula I, but acts via an indirect mechanism and thus reaches its maximum strength of effect only after one hour. Such NHE3 inhibitors acting via different mechanism are suitable for example as combination partners for the present compounds of the invention.

Tetrahydroisoquinolines are also described as inhibitors of the sodium-hydrogen exchanger of subtype 3 (NHE3) in the pending published applications WO03048129 and DE10312963. The patent application WO03055880 describes the related class of tetrahydroisoquinolinium salt compounds as NHE3 inhibitors. It has now been found, surprisingly, that the compounds of the formula I described herein are likewise potent inhibitors of NHE3 and moreover have advantageous pharmacological and pharmacokinetic properties. Thus, the compounds are notable for improved properties such as, for example, a high selectivity for the sodium-hydrogen exchanger with a negligible effect on hERG potassium channels.

NHE3 is found in the body of various species preferentially in the bile, the intestine and the kidney (Larry Fliegel et al., Biochem. Cell. Biol. 76:735-741, 1998), but has also been detected in the brain (E. Ma et al., Neuroscience 79:591-603) both of which are incorporated herein by reference.

On the basis of the NHE-inhibitory properties, the compounds of the formula I and their pharmaceutically acceptable salts are suitable for the prevention and treatment of diseases which are caused by activation or by an activated NHE, and of diseases which are caused secondarily by the NHE-related damage.

Optionally, the NHE inhibitors described herein can be combined with other compounds which also regulate the intracellular pH environment Suitable combinations comprise the formulation with other inhibitors of the enzyme group of carbonic anhydrases and inhibitors of the transport systems that carry bicarbonate ions, such as of the sodium-bicarbonate co-transporter (NBC) or of the sodium-dependent chloride-bicarbonate exchanger, and with other NHE inhibitors with an inhibitory effect on other NHE subtypes, because the pharmacologically relevant pH-regulating effects of the NHE inhibitors described herein can be enhanced or modulated thereby.

The use of compounds of the present invention relates to the prevention and the treatment of acute and chronic diseases in veterinary and human medicine.

The pharmacological effect of the compounds of formula I is such that they lead to an improvement in the respiratory drive. They can therefore be used for the treatment of impaired respiratory conditions with the following clinical conditions and diseases: impaired central respiratory drive (e.g. central sleep apneas, sudden infant death, postoperative hypoxia), muscle-related respiratory impairments, respiratory impairments following long-term ventilation, respiratory impairments associated with altitude adaptation, obstructive and mixed forms of sleep apneas, acute and chronic pulmonary diseases with hypoxia and hypercapnia. The compounds additionally increase the tone of the muscles in the upper respiratory tract, so that snoring is suppressed. Said compounds are therefore advantageously used for the manufacture of a pharmaceutical composition for the prevention and treatment of sleep apneas and muscle-related respiratory impairments and for the preparation of a pharmaceutical composition for the prevention and treatment of snoring.

The combination of an NHE inhibitor of the formula I with a carbonic anhydrase inhibitor (e.g. acetazolamide) is synergistically beneficial in that the latter induces a metabolic acidosis and thereby increases respiratory activity, so that an enhanced effect and lesser amounts of the active ingredient is made possible.

The compounds of the present invention, as a result of their NHE3-inhibitory effect, are able to preserve the cellular energy reserves which are rapidly exhausted during toxic and pathogenic events and thus lead to cell damage or cell death. In this connection, the energy-costly ATP-consuming sodium absorption in the proximal tubule temporarily ceases under the influence of NHE3 inhibitors, and the cell is thus able to survive an acute pathogenic, ischemic or toxic situation. The compounds are therefore suitable as pharmaceuticals for the treatment of ischemic toxicity resulting in, among others, acute renal failure. The compounds are also suitable for the treatment of all chronic renal disorders and types of nephritis which lead, as a consequence of increased protein excretion, to chronic renal failure. Accordingly, the compounds of the formula I are suitable for the preparation of a pharmaceutical composition for the treatment of tissue damage resulting from diabetes, diabetic nephropathy and chronic renal disorders, in particular all renal inflammations (nephritis) which are associated with an increased protein/albumin excretion.

It has also been discovered that the compounds when used according to the present invention also have a mild laxative effect and accordingly can also be used as laxatives when there is a risk of constipation.

The compounds of the present invention can also be used for the prevention and therapy of acute and chronic disorders of the intestinal tract which are induced for example by ischemic states in the intestinal region and/or by subsequent reperfusion or by inflammatory states and events. Such complications may arise for example through deficient intestinal peristalsis as are frequently to be observed for example following surgical interventions, associated with constipation or greatly reduced intestinal activity.

It is also possible to prevent the formation of gallstones with the compounds of the present invention. Moreover, the NHE inhibitors of the present invention are also generally suitable for the treatment of diseases caused by ischemia and by reperfusion.

The compounds of the present invention are, as a result of their pharmacological properties, suitable as anti-arrhythmic pharmaceuticals. Owing to their cardioprotective component, the NHE inhibitors are outstandingly suitable for the prophylaxis of infarction and for the treatment of infarction, and for the treatment of angina pectoris, in which case they inhibit or greatly reduce preventively the pathophysiological processes associated with the development of damage induced by ischemia, in particular with the triggering of cardiac arrhythmias induced by ischemia.

Because of their protective effects against pathological hypoxic and ischemic situations, the compounds of the formula I used according to the invention can, as a result of inhibition of the cellular $Na^+/H^+$ exchange mechanism, be used as pharmaceuticals for the treatment of all acute or chronic damage induced by ischemia or diseases induced primarily or secondarily thereby.

This also relates to the use as pharmaceuticals for surgical interventions. Thus, the compounds of the invention can be used in organ transplantations, in which case the compounds can be used both to protect the organs in the donor before and during removal, to protect removed organs for example during treatment with or storage thereof in physiological bath fluids, as well as during transfer into the recipient organism pretreated with compounds of the formula I.

The compounds are likewise valuable pharmaceuticals with a protective effect for carrying out angioplastic surgical interventions for example on the heart as well as on peripheral organs and vessels.

In accordance with their protective effect against damage induced by ischemia, the compounds are also suitable as pharmaceuticals for the treatment of ischemias of the nervous system, especially of the CNS, being suitable for example for the treatment of stroke or of cerebral edema.

Since NHE inhibitors of human tissue and organs protect effectively not only against damage caused by ischemia and reperfusion but also against the cytotoxic effect of pharmaceuticals like those used in particular in cancer therapy and the therapy of autoimmune diseases, combined administration thereof with compounds of the formula I is suitable for reducing or suppressing the cytotoxic effects of a therapy. The reduction in the cytotoxic effects, especially the cardiotoxicity, as a result of comedication with NHE inhibitors makes it additionally possible to increase the dose of the cytotoxic therapeutic agents and/or to prolong the medication with such pharmaceuticals. The therapeutic benefit of such a cytotoxic therapy can be increased considerably by combination with NHE inhibitors.

The compounds of the formula I are particularly suitable for improving therapy with pharmaceuticals which have an unwanted cardiotoxic component.

In accordance with their protective effect against damage induced by ischemia, the compounds are also suitable as pharmaceuticals for the treatment of ischemias of the nervous system, especially of the central nervous system, being suitable for example for the treatment of stroke or of cerebral edema.

The compounds of the formula I are also suitable for the therapy and prophylaxis of disorders and impairments induced by overexcitability of the central nervous system, in particular for the treatment of epileptiform disorders, centrally induced clonic and tonic spasms, states of mental depression, anxiety disorders and psychoses. The NHE inhibitors of the invention may in this connection be used alone or in combination with other substances having antiepileptic activity or antipsychotic active ingredients, or carbonic anhydratase inhibitors, for example with acetazolamide, and with further inhibitors of NHE or of the sodium-dependent chloride-bicarbonate exchanger (NCBE).

In addition, the compounds of the invention of the formula I are likewise suitable for the treatment of types of shock such as, for example, of allergic, cardiogenic, hypovolemic and bacterial shock.

The compounds of the formula I can likewise be used for the prevention and treatment of thrombotic disorders because, as NHE inhibitors, they are able to inhibit both platelet aggregation itself. In addition, they are able to inhibit or prevent the excessive release of mediators of inflammation and coagulation, in particular of von Willebrand factor and thrombogenic selectin proteins, which takes place following ischemia and reperfusion. It is thus possible to reduce and eliminate the pathogenic effect of thrombogenic and inflammation-relevant factors. The NHE inhibitors of the present invention can therefore be combined with further anticoagulant and/or thrombolytic active ingredients such as, for example, recombinant or natural tissue plasminogen activator, streptokinase, urokinase, acetylsalicylic acid, thrombin antagonists, factor Xa antagonists, drugs with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonic anhydratase such as, for example, with acetazolamide is particularly beneficial.

The NHE inhibitors of the invention are additionally notable for a strong inhibitory effect on the proliferation of cells, for example fibroblast cell proliferation and the proliferation of smooth vascular muscle cells. The compounds of the formula I are therefore suitable as valuable therapeutic agents for diseases in which cell proliferation represents a primary or secondary cause, and can therefore used as antiatherosclerotics, agents against chronic renal failure, cancers. They can thus be used for the treatment of organ hypertrophies and hyperplasias, for example of the heart and of the prostate. Compounds of the formula I are therefore suitable for the prevention and treatment of heart failure (congestive heart failure=CHF) and for the treatment and prevention of prostate hyperplasia or prostate hypertrophy.

NHE inhibitors are further notable for a retardation or prevention of fibrotic disorders. They are thus suitable as outstanding agents for the treatment of fibroses of the heart, and of pulmonary fibrosis, hepatic fibrosis, renal fibrosis and other fibrotic disorders.

Since NHE is significantly elevated in essential hypertensives, the compounds of the formula I are suitable for the prevention and treatment of high blood pressure and of cardiovascular disorders. They can be used in this connection alone or with a suitable combination partner for the treatment of high blood pressure and for the treatment of cardiovascular disorders. Thus, for example, one or more diuretics having a thiazide-like action, loop diuretics, aldosterone and pseudoaldosterone antagonists such as hydrochlorothiazide, indapamide, polythiazide, furosemide, piretanide, torasemide, bumetamide, amiloride, triamterene, spironolactone or eplerone, can be combined with compounds of the formula I. The NHE inhibitors of the present invention can moreover be used in combination with calcium antagonists such as verapamil, diltiazem, amlodipine or nifedipine, and with ACE inhibitors such as, for example, ramipril, enalapril, lisinopril, fosinopril or captopril. Further beneficial combination partners are also β blockers such as metoprolol, albuterol etc., antagonists of the angiotensin receptor and its receptor subtypes such as losartan, irbesartan, valsartan, omapatrilat, gernopatrilat, endothelin antagonists, renin inhibitors, adenosine receptor agonists, inhibitors and activators of potassium channels such as glibenclamide, glimepiride, diazoxide, cromokalim, minoxidil and derivatives thereof, activators of the mitochondrial ATP-sensitive potassium channel (mitoK(ATP) channel), inhibitors of further potassium channels such as of Kv1.5 etc.

As a result of their antiinflammatory effect, NHE inhibitors of the invention can be used as antiinflammatory drugs. Mechanistically notable in this connection is the inhibition of the release of mediators of inflammation. The compounds can thus be used alone or in combination with an anti-inflammatory drug for the prevention or treatment of chronic and acute inflammatory disorders. Combination partners which are advantageously used are steroidal and non-steroidal antiinflammatory drugs.

It has additionally been found that NHE inhibitors show a beneficial effect on serum lipoproteins. They can therefore be used for the prophylaxis and regression of atherosclerotic lesions by eliminating a causal risk factor. These include not only the primary hyperlipidemias, but also certain secondary hyperlipidemias like those occurring for example in association with diabetes. In addition, NHE inhibitors lead to a marked reduction in the infarctions induced by metabolic abnormalities and in particular to a significant reduction in the induced infarct size and its severity. NHE inhibitors of the formula I are therefore advantageously used for the manufacture of a medicament for the treatment of hypercholesterolemia; for the manufacture of a medicament for the prevention of atherogenesis; for the manufacture of a medicament for the prevention and treatment of atherosclerosis, for the manufacture of a medicament for the prevention and treatment of diseases induced by elevated cholesterol levels, for the manufacture of a medicament for the prevention and treatment of diseases induced by endothelial dysfunction, for the manufacture of a medicament for the prevention and treatment of atherosclerosis-induced hypertension, for the manufacture of a medicament for the prevention and treatment of atherosclerosis-induced thromboses, for the manufacture of a medicament for the prevention and treatment of ischemic damage induced by hypercholesterolemia and endothelial dysfunction, and postischemic reperfusion damage, for the manufacture of a medicament for the prevention and treatment of cardiac hypertrophies and cardiomyopathies and of congestive heart failure (CHF), for the manufacture of a medicament for the prevention and treatment of coronary vasospasms and myocardial infarction induced by hypercholesterolemia and endothelial dysfunction, for the manufacture of a medicament for the treatment of said disorders in combinations with hypotensive substances, preferably with angiotension converting enzyme (ACE) inhibitors and angiotensin receptor antagonists. Combination of an NHE inhibitor of the formula I with an active ingredient which lowers the blood lipid level, preferably with an HMG-CoA reductase inhibitor (e.g. lovastatin or pravastatin), where the latter brings about a hypolipidemic effect and thus increases the hypolipidemic properties of the NHE inhibitor of the formula I, represents a favorable combination with enhanced effect and reduced use of active ingredient.

Thus, NHE inhibitors lead to effective protection from endothelial damage of various origins. With this protection of vessels against the syndrome of endothelial dysfunction, NHE inhibitors are valuable pharmaceuticals for the prevention and treatment of coronary vasospasms, peripheral vascular diseases, especially intermittent claudicating, parthenogenesis and atherosclerosis, left-ventricular hypertrophy and dilated cardiomyopathy, and thrombotic disorders.

NHE inhibitors are additionally suitable for the treatment of non-insulin-dependent diabetes (NIDDM), in which case for example insulin resistance is restrained. It may in this connection be beneficial, for enhancing the antidiabetic efficacy and quality of the effect of the compounds of the invention, to combine them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute antidiabetic effects, NHE inhibitors counteract the development of late complications of diabetes and can therefore be used as pharmaceuticals for the prevention and treatment of late damage from diabetes, such as diabetic nephropathy, diabetic neuropathy, diabetic retinopathy, diabetic cardiomyopathy and other disorders arising as a consequence of diabetes. They can in this connection be advantageously combined with the antidiabetic pharmaceuticals described above under NIDDM treatment. Combination with a beneficial dosage form of insulin may be particularly important in this connection.

NHE inhibitors show, besides the protective effects against acute ischemic events and the subsequent equally acutely stressing reperfusion events, also direct therapeutically utilizable effects against disorders and impairments of the whole mammalian organism which are associated with the manifestations of the chronically progressive aging process and which are also independent of acute states of defective blood supply and may also occur under normal, non-ischemic conditions. These pathological, age-related manifestations induced over the long aging period, such as disease, invalidity and death, which can now be made amenable to treatment with NHE inhibitors, are disorders and impairments which are essentially caused by age-related changes in vital organs and the function thereof and become increasingly important in the aging organism.

Disorders associated with an age-related functional impairment, with age-related manifestations of wear of organs, are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. An important function and a measure of the maintenance of the reactivity of vessels is the blockade or retardation of the age-related progression of endothelial dysfunction, which can be eliminated highly significantly by NHE inhibitors. NHE inhibitors are thus outstandingly suitable for the treatment and prevention of the age-related progression of endothelial dysfunction, in particular of intermittent claudication. NHE inhibitors are thus outstandingly suitable in addition for the treatment and prevention of heart failure, of congestive heart failure (CHF) and for the treatment and in particular for the prevention of age-related types of cancer.

Combination with hypotensive medicaments such as with ACE inhibitors, angiotensin receptor antagonists, diuretics, $Ca^{2+}$ antagonists etc. or with metabolism-normalizing medicaments such as cholesterol-lowering agents comes into consideration in this connection. The compounds of the formula I are thus suitable for the prevention of age-related tissue lesions and for maintaining health and prolonging life while maintaining a high quality of life.

The compounds of the invention are effective inhibitors of the cellular sodium-proton antiporter (Na/H exchanger) which in a large number of disorders (essential hypertension, atherosclerosis, diabetes etc.) is also elevated in cells which are easily amenable to measurements, such as, for example, in erythrocytes, platelets or leukocytes. The compounds used according to the invention are therefore suitable as excellent and simple scientific tools, for example in their use as diagnostic aids for diagnosing and distinguishing particular types of hypertension, but also of atherosclerosis, of diabetes and the late complications of diabetes, proliferative disorders etc.

NHE3 inhibitors are further suitable for the treatment of diseases (human and veterinary) induced by bacteria and by protozoa. In the context of diseases caused by protozoa, particular mention should be made of malarial diseases of humans and coccidiosis of poultry.

The compounds are also suitable as agents for controlling sucking parasites in human and veterinary medicine and in crop protection. Preference is given in this connection to the use as agents against blood-sucking parasites in human and veterinary medicine.

Said compounds are therefore advantageously used alone or in combination with other pharmaceuticals or active ingredients for the preparation of a pharmaceutical composition for the treatment or prophylaxis of disorders of the pulmonary, lung and respiratory systems, of respiratory disorders, sleep-related respiratory disorders, sleep apneas, of snoring, of acute and chronic renal disorders, of acute renal failure and of chronic renal failure, of impairments of bowel function, of high blood pressure, of essential hypertension, of central nervous system disorders, of disorders resulting from CNS overexcitability, epilepsy and centrally induced spasms or of anxiety states, depressions and psychoses, of ischemic states of the peripheral or central nervous system or of stroke, of acute and chronic damage and disorders of peripheral organs or limbs caused by ischemic or reperfusion events, of atherosclerosis, of impairments of lipid metabolism, of thromboses, of impairments of biliary function, of infestation by ectoparasites, of disorders resulting from endothelial dysfunction, of protozoan diseases, of malaria, for the preservation and storage of organ transplants for surgical procedures, for use in surgical operations and organ transplants or for the treatment of diabetes and tissue damage from diabetes or of diseases in which cell proliferation represents a primary or secondary cause, and for maintaining health and prolonging life.

Also claimed is a medicine for human, veterinary or phytoprotective use comprising an effective amount of a compound of the formula I and/or pharmaceutically acceptable salts thereof, together with pharmaceutically acceptable carriers and additives, alone or in combination with other pharmacological active ingredients or pharmaceuticals.

Pharmaceuticals which comprise a compound of the formula I or the pharmaceutically acceptable salts thereof can be administered for example orally, parenterally, intramuscularly, subcutaneously, intravenously, rectally, nasally, by inhalation, or by a suitable transcutaneous dosage form, the preferred administration depending on the respective manifestation of the disorder. The compounds of the formula I can be used alone or together with pharmaceutical excipients, specifically both in veterinary and in human medicine and in crop protection. The pharmaceuticals comprise active ingredients of the formula I and/or pharmaceutically acceptable salts thereof generally in an amount of from 0.01 mg to 1 g per dose unit.

The skilled worker is familiar on the basis of his expert knowledge with the excipients suitable for the desired pharmaceutical formulation. Besides solvents, gel formers, suppository bases, tablet excipients and other active ingredient carriers it is possible to use for example antioxidants, dispersants, emulsifiers, antifoams, masking flavors, preservatives, solubilizers or colorants.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch.

It is moreover possible for the preparation to take place both as dry and as wet granules. Examples of suitable oily carriers or solvents are vegetable or animal oils, such as sunflower oil or fish liver oil.

For subcutaneous, percutaneous or intravenous administration, the active compounds used are converted, if desired with the substances usual for this purpose, such as solubilizers, emulsifiers or further excipients, into solution, suspension or emulsion. Examples of suitable solubilizers are: water, physiological saline or alcohols, e.g. ethanol, propanol, glycerol, as well as sugar solutions such as glucose or mannitol solutions, or also a mixture of the various solvents mentioned.

Suitable as pharmaceutical formulation for administration in the form of aerosols or sprays are for example solutions, suspensions or emulsions of the active ingredient of the formula I in a pharmaceutically acceptable solvent such as, in particular, ethanol or water, or a mixture of such solvents. The formulation may, if required, also comprise other pharmaceutical excipients such as surfactants, emulsifiers and stabilizers, and a propellant gas. Such a preparation normally comprises the active ingredient in a concentration of about 0.1 to 10, in particular of about 0.3 to 3% by weight.

The dosage of the active ingredient of the formula I to be administered and the frequency of administration depend on the potency and duration of action of the compounds used; additionally also on the nature and severity of the disease to be treated and on the gender, age, weight and individual response of the mammal to be treated.

On average, the daily dose of a compound of the formula I for a patient weighing about 75 kg is at least 0.001 mg/kg, preferably 0.1 mg/kg, to a maximum of 30 mg/kg, preferably 1 mg/kg, of body weight. In acute situations, for example immediately after suffering apneic states at high altitude, higher doses may also be necessary. Up to 300 mg/kg per day may be necessary in particular on i.v. administration, for example for an infarct patient in intensive care. The daily dose can be divided into one or more, for example up to 4, single doses.

It will be appreciated that every suitable combination of the compounds of the invention with one or more of the aforementioned compounds and optionally one or more other pharmacologically active substances is regarded as falling within the scope of the claims of the present invention. The examples detailed below are provided to better describe and more specifically set forth the compounds, processes and methods of the present invention, but for obvious reasons cannot describe all of them. It is to be recognized that they are for illustrative purposes only however, and should not be interpreted as limiting the spirit and scope of the invention as later recited by the claims that follow.

EXAMPLES

The following is a list of abbreviations used in the description and recitation of the experiments and examples that follow.

ADMET adsorption-distribution-metabolism-excretion-toxicology
MeOH methanol
MPRC Cartridge L-026-30; S160 40-63 μm; Super Vario Flash; max. press. 3 bar Götec-Labortechnik GmbH
solv. solvent
THF tetrahydrofuran

Example 1

6,8-Dichloro-2-methyl-4-[N-(2-ethoxy-3,4-dioxocyclobuten-1-yl)amino]phenyl-1,2,3,4-tetrahydroisoquinoline

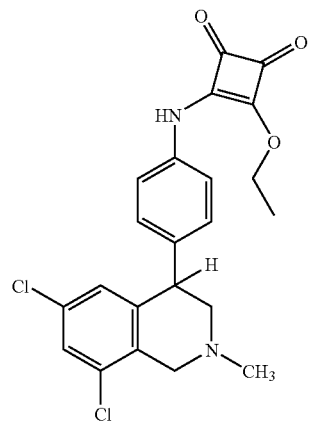

320 mg of 1,2-diethoxy-3,4-dioxo-1-cyclobutene (diethyl squarate) were added to a solution of 0.58 g of 4-(4-aminophenyl)-6,8-dichloro-2-methyl-1,2,3,4-tetrahydroisoquinoline in 40 ml of anhydrous ethanol and, after stirring at room temperature for 48 hours, the precipitate was filtered off. Colorless crystalline solid, decomposition point: 240° C.

Example 2

6,8-Dichloro-2-methyl-4-[3N-(2-ethoxy-3,4-dioxocyclobuten-1-yl)amino]phenyl-1,2,3,4-tetrahydroisoquinoline

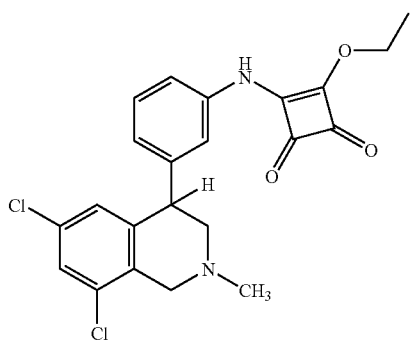

69.2 mg of 1,2-diethoxy-3,4-dioxo-1-cyclobutene (diethyl squarate) were added to a solution of 0.125 g of 4-(3-aminophenyl)-6,8-dichloro-2-methyl-1,2,3,4-tetrahydroisoquinoline in 40 ml of anhydrous ethanol and, after stirring at room temperature for 48 hours, the solvent was distilled under reduced pressure in a rotavapor. The oily residue was separated by MPRC chromatography with a solvent mixture of equal parts by volume of ethyl acetate and toluene. Yellow crystalline solid, m.p. 188-194° C.

Example 3

6,8-Dichloro-2-methyl-4-[2N-(2-ethoxy-3,4-dioxo-cyclobuten-1-yl)amino]phenyl-1,2,3,4-tetrahydroisoquinoline

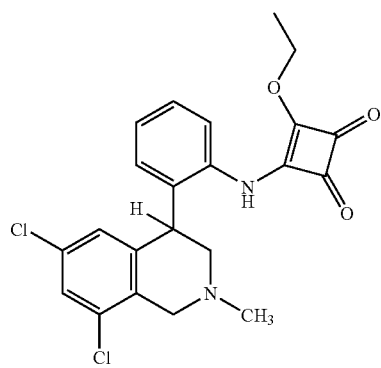

0.07 ml of 1,2-diethoxy-3,4-dioxo-1-cyclobutene (diethyl squarate) was added to a solution of 150 mg of 4-(2-aminophenyl)-6,8-dichloro-2-methyl-1,2,3,4-tetrahydroisoquinoline in 10 ml of anhydrous ethanol and, after stirring at room temperature for 70-80 hours, the solvent was removed by distillation under reduced pressure in a rotavapor. The residue was dissolved in a little ethyl acetate and left to stand at room temperature for about 4 hours and in a refrigerator at 0-5° C. overnight. The crystalline precipitate was filtered off. Colorless crystalline solid, m.p. 152-155° C.

Example 4

6,8-Dichloro-2-methyl-4(S)-[4N-(2-ethoxy-3,4-dioxocyclobuten-1-yl)amino]phenyl-1,2,3,4-tetrahydroisoquinoline

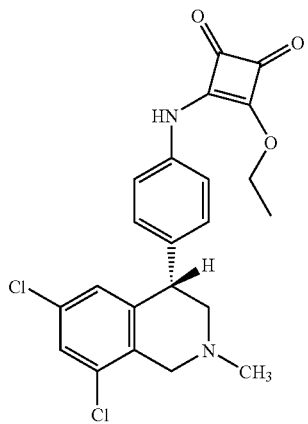

0.28 g of 1,2-diethoxy-3,4-dioxo-1-cyclobutene (diethyl squarate) was added to a solution of 0.51 g of 4(S)-(4-aminophenyl)-6,8-dichloro-2-methyl-1,2,3,4-tetrahydroisoquinoline in 40 ml of anhydrous ethanol and stirred at room temperature for 6 hours, and the solvent was removed by distillation under reduced pressure in a rotavapor. The residue crystallized under diisopropyl ether. Colorless crystalline solid, m.p. 208-212° C.

Example 5

6,8-Dichloro-2-methyl-4(S)-[3N-(2-ethoxy-3,4-dioxocyclobuten-1-yl)amino]phenyl-1,2,3,4-tetrahydroisoquinoline

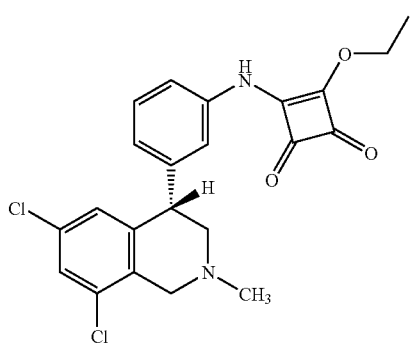

0.2 g of 1,2-diethoxy-3,4-dioxo-1-cyclobutene (diethyl squarate) was added to a solution of 0.366 g of 4(S)-(3-aminophenyl)-6,8-dichloro-2-methyl-1,2,3,4-tetrahydroisoquinoline in 25 ml of anhydrous ethanol and stirred at room temperature for 6 hours, and the solvent was removed by distillation under reduced pressure in a rotavapor. The residue crystallized under diisopropyl ether. Colorless crystalline solid, m.p. 198-202° C.

Example 6

6,8-Dichloro-2-methyl-4(R)-[2N-(2-ethoxy-3,4-dioxocyclobuten-1-yl)amino]phenyl-1,2,3,4-tetrahydroisoquinoline

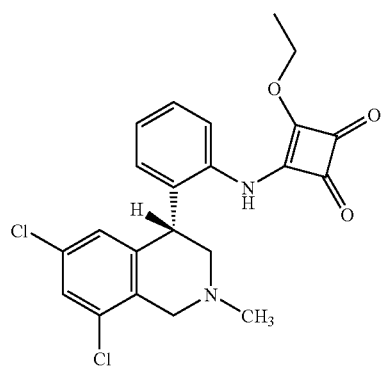

0.309 ml of 1,2-diethoxy-3,4-dioxo-1-cyclobutene (diethyl squarate) was added to a solution of 0.64 g of 4(R)-(2-aminophenyl)-6,8-dichloro-2-methyl-1,2,3,4-tetrahydroisoquinoline in 40 ml of anhydrous ethanol and stirred at room temperature for 50-60 hours, and the solvent was removed by distillation under reduced pressure in a rotavapor. The residue crystallized under diisopropyl ether. Colorless crystalline solid, m.p. 205-210° C.

Example 7

6,8-Dichloro-2-methyl-4-[4N-(2-hydroxy-3,4-dioxo-cyclobuten-1-yl)amino]phenyl-1,2,3,4-tetrahydroisoquinoline hydrochloride

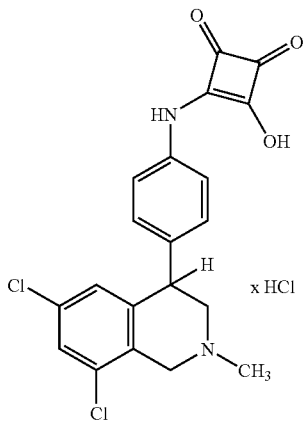

A solution of 97.3 mg of lithium hydroxide hydrate (LiOH×H$_2$O) in 15 ml of H$_2$O was added to a solution of 100 mg of 6,8-dichloro-2-methyl-4-[4N-(2-ethoxy-3,4-dioxocyclobuten-1-yl)amino]phenyl-1,2,3,4-tetrahydroisoquinoline (Example 1) in 15 ml of THF, and the mixture was boiled with a reflux condenser for 15 hours. The THF was evaporated in a rotavapor and the aqueous solution was treated with 2N HCl. The resulting suspension was stirred at room temperature for about 1 hour and the precipitate was filtered off. Colorless crystalline product, m.p. >310° C.

Example 8

6,8-Dichloro-2-methyl-4-[3N-(2-hydroxy-3,4-dioxo-cyclobuten-1-yl)amino]phenyl-1,2,3,4-tetrahydroisoquinoline hydrochloride

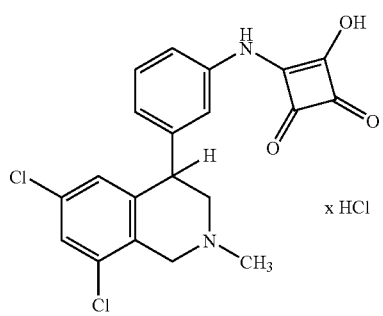

was obtained in analogy to the method described in Example 7 from 6,8-dichloro-2-methyl-4-[3N-(2-ethoxy-3,4-dioxocyclobuten-1-yl)amino]phenyl-1,2,3,4-tetrahydroisoquinoline. Solid which sublimes above 110° C.

Example 9

6,8-Dichloro-2-methyl-4-[2N-(2-hydroxy-3,4-dioxo-cyclobuten-1-yl)amino]phenyl-1,2,3,4-tetrahydroisoquinoline hydrochloride

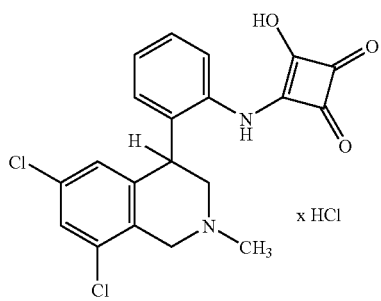

was obtained in analogy to the method described in Example 7 from 6,8-dichloro-2-methyl-4-[2N-(2-ethoxy-3,4-dioxocyclobuten-1-yl)amino]phenyl-1,2,3,4-tetrahydroisoquinoline. Crystalline solid, m.p. >310° C.

Example 10

6,8-Dichloro-2-methyl-4-[4N-(2-amino-3,4-dioxocyclobuten-1-yl)amino]phenyl-1,2,3,4-tetrahydroisoquinoline

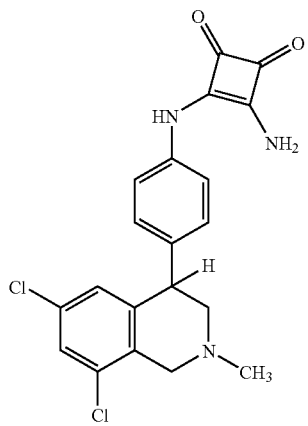

100 mg of a suspension of 6,8-dichloro-2-methyl-4-[4N-(2-ethoxy-3,4-dioxocyclobuten-1-yl)amino]phenyl-1,2,3,4-tetrahydroisoquinoline (Example 1) in 3 ml of methanol was stirred with 3 ml of a methanolic ammonia solution at room temperature for 3 hours, and the crystals were filtered off and washed with a little methanol. Colorless crystalline substance, m.p. >310° C.

Example 11

6,8-Dichloro-2-methyl-4-[3N-(2-amino-3,4-dioxocyclobuten-1-yl)amino]phenyl-1,2,3,4-tetrahydroisoquinoline

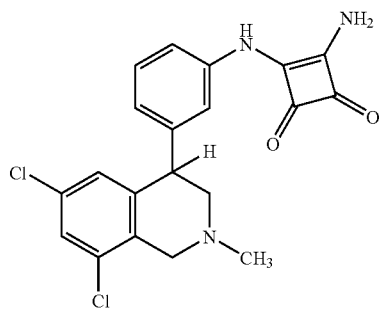

was obtained in analogy to the method described in Example 10 by reacting 6,8-dichloro-2-methyl-4-[3N-(2-ethoxy-3,4-dioxocyclobuten-1-yl)amino]phenyl-1,2,3,4-tetrahydroisoquinoline with methanolic ammonia solution. Colorless crystalline substance, m.p. >310° C.

Example 12

6,8-Dichloro-2-methyl-4-[2N-(2-amino-3,4-dioxocyclobuten-1-yl)amino]phenyl-1,2,3,4-tetrahydroisoquinoline

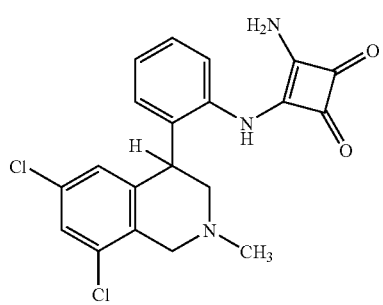

was obtained in analogy to the method described in Example 10 by reacting 6,8-dichloro-2-methyl-4-[2N-(2-ethoxy-3,4-dioxocyclobuten-1-yl)amino]phenyl-1,2,3,4-tetrahydroisoquinoline with methanolic ammonia solution. Colorless crystalline substance, decomposition point above 170° C.

Example 13

6,8-Dichloro-2-methyl-4(S)-[4N-(2-amino-3,4-dioxocyclobuten-1-yl)amino]phenyl-1,2,3,4-tetrahydroisoquinoline

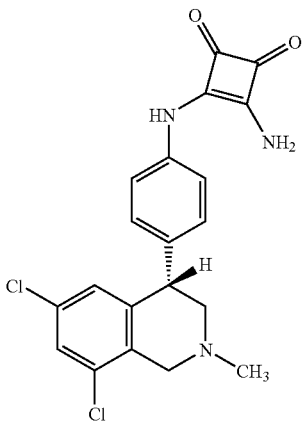

was obtained in analogy to the method described in Example 10 by reacting 6,8-dichloro-2-methyl-4(S)-[4N-(2-ethoxy-3,4-dioxocyclobuten-1-yl)amino]phenyl-1,2,3,4-tetrahydroisoquinoline with methanolic ammonia solution. Colorless crystalline substance, m.p. >310° C.

Example 14

6,8-Dichloro-2-methyl-4(S)-[3N-(2-amino-3,4-dioxocyclobuten-1-yl)amino]phenyl-1,2,3,4-tetrahydroisoquinoline

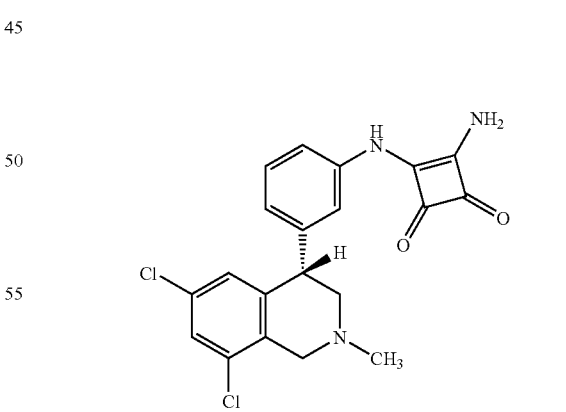

was obtained in analogy to the method described in Example 10 by reacting 6,8-dichloro-2-methyl-4(S)-[3N-(2-ethoxy-3,4-dioxocyclobuten-1-yl)amino]phenyl-1,2,3,4-tetrahydroisoquinoline with methanolic ammonia solution. Colorless crystalline substance, decomposition point above 190° C.

Example 15

6,8-Dichloro-2-methyl-4(R)-[2N-(2-amino-3,4-di-oxocyclobuten-1-yl)amino]phenyl-1,2,3,4-tetrahydroisoquinoline

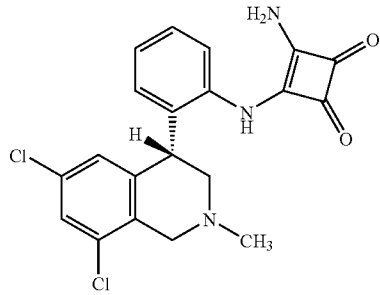

was obtained in analogy to the method described in Example 10 by reacting 6,8-dichloro-2-methyl-4(R)-[2N-(2-ethoxy-3,4-dioxocyclobuten-1-yl)amino]phenyl-1,2,3,4-tetrahydroisoquinoline with methanolic ammonia solution. Colorless crystalline substance, m.p. 215-220° C.

Example 16

Method for the Preparation of 4-[N-(2-amino-3,4-dioxocyclobuten-1-yl)amino]phenyl-1,2,3,4-tetrahydroisoquinolines (XIX)

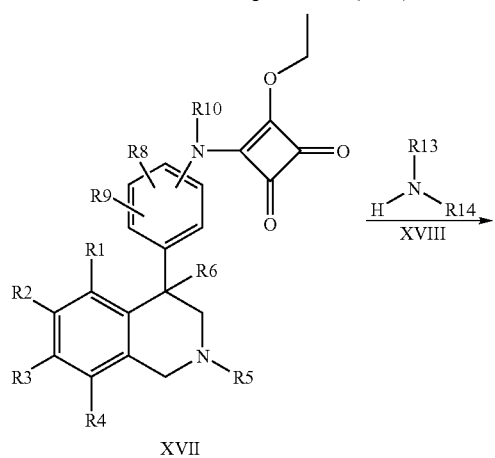

XVII

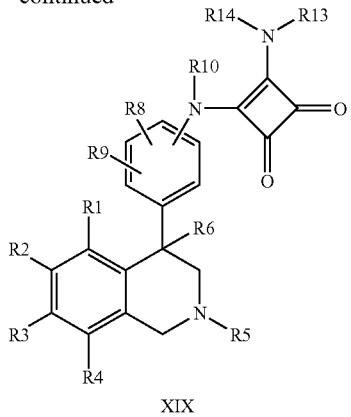

XIX 1-2 mmol of amine of the formula XVIII were added to a solution or suspension of 1 mmol of a squaric ester of the formula XVII in 50-100 ml of anhydrous methanol, and the reaction mixture was stirred at room temperature or with gentle heating for 3-24 hours, following the progress of the reaction by thin-layer chromatography or LC-MS analysis. The final product XIX was removed by filtration and washed with a little methanol if the compound separated as precipitate out of the solution (variant a).

If the final product precipitate could not be isolated as precipitate, the solvent was removed by distillation under reduced pressure in a rotavapor, and the usually oily residue was induced to crystallize under a solvent such as, for example, under diisopropyl ether (variant b).

In other cases, the residue was purified by preparative MPRC chromatography to take place (variant c), using a mixture A) of 10 parts by volume of methylene chloride or B) 1 part of methanol or a mixture of 10 parts by volume of ethyl acetate, 5 parts by volume of n-heptane, 5 parts by volume of methylene chloride, 5 parts by volume of methanol and 1 part by volume of 28% strength ammonia.

The examples of the invention indicated in the following table were prepared in accordance with this method.

| Example | Name | Formula XIX | Reaction conditions | m.p. ° C. |
|---|---|---|---|---|
| 17 | 6,8-dichloro-2-methyl-4-[4N-(2-N-cyclohexyl-N-methylamino-3,4-dioxocyclobuten-1-yl)amino]phenyl-1,2,3,4-tetrahydroisoquinoline | | Variant a | 260-265 |

-continued

| Example | Name | Formula XIX | Reaction conditions | m.p. ° C. |
|---|---|---|---|---|
| 18 | 6,8-dichloro-2-methyl-4-[4N-(2-dimethylamino-3,4-dioxocyclobuten-1-yl)amino]phenyl-1,2,3,4-tetrahydroisoquinoline | | Variant b, crystallization from ethyl acetate | 208-214 |
| 19 | 6,8-dichloro-2-methyl-4-[4N-(2-diethylamino-3,4-dioxocyclobuten-1-yl)amino]phenyl-1,2,3,4-tetrahydroisoquinoline | | Variant b, crystallization from a mixture of ethyl acetate and diisopropyl ether | 275-280 |
| 20 | 6,8-dichloro-2-methyl-4(S)-[4N-(2-dimethylamino-3,4-dioxocyclobuten-1-yl)amino]phenyl-1,2,3,4-tetrahydroisoquinoline | | Variant b, crystallizaion from ethyl acetate | 240-247 |

-continued

| Example | Name | Formula XIX | Reaction conditions | m.p. ° C. |
|---|---|---|---|---|
| 21 | 6,8-dichloro-2-methyl-4(R)-[2N-(2-dimethylamino-3,4-dioxocyclobuten-1-yl)amino]phenyl-1,2,3,4-tetrahydroisoquinoline | | Variant c, MPRC in B), then crystallization from ethyl acetate | 236-240 |
| 22 | 6,8-dichloro-2-methyl-4(S)-[3N-(2-dimethylamino-3,4-dioxocyclobuten-1-yl)amino]phenyl-1,2,3,4-tetrahydroisoquinoline | | Variant c, MPRC in B), then crystallization from ethyl acetate | decomposition point 140° C. |
| 23 | 6,8-dichloro-2-methyl-4(S)-[4N-(2N-(1-butyl)-N-methylamino-3,4-dioxocyclobuten-1-yl)amino]phenyl-1,2,3,4-tetrahydroisoquinoline | | Variant c, MPRC in B), then crystallization from diisopropyl ether | 145-150 |
| 24 | 6,8-dichloro-2-methyl-4-[4N-(2-dipropylamino-3,4-dioxocyclobuten-1-yl)amino]phenyl-1,2,3,4-tetrahydroisoquinoline | | Variant c, MRPC in B) | decomposition point at 130° C. |

-continued

| Example | Name | Formula XIX | Reaction conditions | m.p. ° C. |
|---|---|---|---|---|
| 25 | 6,8-dichloro-2-methyl-4-[4N-(2-(N-isobutyl-N-methylamino)-3,4-dioxocyclobuten-1-yl)amino]phenyl-1,2,3,4-tetrahydroisoquinoline | | Variant c, MPRC in B) | >310 |
| 26 | 6,8-dichloro-2-methyl-4-[4N-(2-(N-methoxyethyl)-N-methylamino)-3,4-dioxocyclobuten-1-yl)amino]phenyl-1,2,3,4-tetrahydroisoquinoline | | Variant c, MPRC in B), then crystallization from ethyl acetate | 206-210 |
| 27 | 6,8-dichloro-2-methyl-4(S)-[4N-(2-diethylamino-3,4-dioxocyclobuten-1-yl)amino]phenyl-1,2,3,4-tetrahydroisoquinoline | | Variant c, MPRC in B), then crystallization from diisopropyl ether/ethyl acetate | 220-225 |

-continued

| Example | Name | Formula XIX | Reaction conditions | m.p. ° C. |
|---|---|---|---|---|
| 28 | 6,8-dichloro-2-methyl-4(S)-[4N-(2-(N-isopropyl-N-methylamino)-3,4-dioxocylcobuten-1-yl)amino]phenyl-1,2,3,4-tetrahydro-isoquinoline | | Variant c, MPRC in B), then crystallization from diisopropyl, ether/ethyl acetate | 165-175 (decomposition) |
| 29 | 6,8-dichloro-2-methyl-4-[4N-(2-(N-cyclopropylmethyl-N-propylamino)-3,4-dioxocyclobuten-1-yl)amino]phenyl-1,2,3,4-tetrahydro-isoquinoline | | Variant c, MPRC in A), then crystallization from water | 134-144 |
| 30 | 6,8-dichloro-2-methyl-4(S)-[3N-(2-diethylamino)-3,4-dioxocyclobuten-1-yl)amino]phenyl-1,2,3,4-tetrahydro-isoquinoline | | Variant c, MPRC in A), then crystallization from water | 125-135 |
| 31 | 6,8-dichloro-2-methyl-4(S)-[3N-(2-N-methyl-N-isopropyl)amino-3,4-dioxocyclobuten-1-yl)amino]phenyl-1,2,3,4-tetrahydro-isoquinoline | | Variant c, MPRC in A), then crystallization from water | 135-150 |

-continued

| Example | Name | Formula XIX | Reaction conditions | m.p. ° C. |
|---|---|---|---|---|
| 32 | 6,8-dichloro-2-methyl-4(S)-[4N-(2N-ethyl-N-isopropyl)amino-3,4-dioxocyclobuten-1-yl)amino]phenyl-1,2,3,4-tetrahydroisoquinoline | | Variant c, MPRC in B), then crystallization from diisopropyl ether/ethyl acetate, then from water | 160-190 |
| 33 | 6,8-dichloro-2-methyl-4(S)-[3N-(2-N-methyl-N-propyl-amino)-3,4-dioxocyclobuten-1-yl)amino]phenyl-1,2,3,4-tetrahydroisoquinoline | | Variant c, MPRC in A), then crystallization from water | 135-140 |
| 34 | 6,8-dichloro-2-methyl-4(S)-[3N-(2-N-pyrrolidino-3,4-dioxocyclobuten-1-yl)amino]phenyl-1,2,3,4-tetrahydroisoquinoline | | Variant c, MPRC in A), then crystallization from water | 138-143 |

-continued

| Example | Name | Formula XIX | Reaction conditions | m.p. ° C. |
|---|---|---|---|---|
| 35 | 6,8-dichloro-2-methyl-4(S)-[4N-(2-N-cyclopropylamino)-3,4-dioxocyclobuten-1-yl)amino]phenyl-1,2,3,4-tetrahydroisoquinoline | 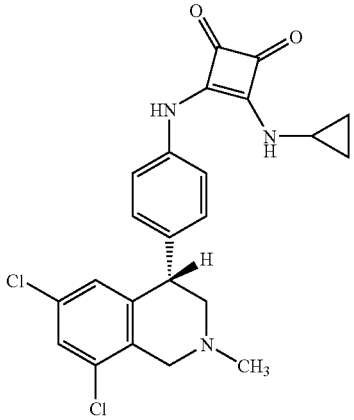 | Variant a | 280-285 |
| 36 | 6,8-dichloro-2-methyl-4(S)-[4N-(2-N-pyrrolidino-3,4-dioxocyclobuten-1-yl)amino]phenyl-1,2,3,4-tetrahydroisoquinoline | 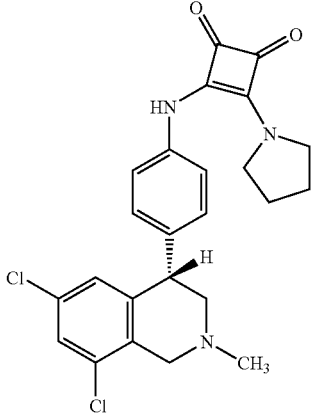 | Variant a | 264-270 |
| 37 | 6,8-dichloro-2-methyl-4(R)-[2N-(2-N-methyl-N-propyl-amino)-3,4-dioxocyclobuten-1-yl)amino]phenyl-1,2,3,4-tetrahydroisoquinoline | 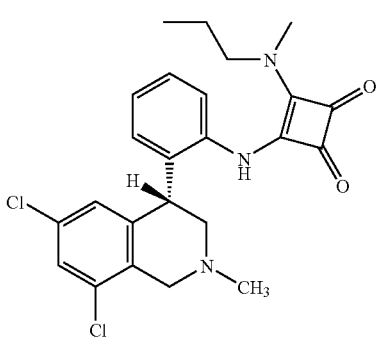 | Variant a | 236-240 |

-continued

| Example | Name | Formula XIX | Reaction conditions | m.p. ° C. |
|---------|------|-------------|---------------------|-----------|
| 38 | 6,8-dichloro-2-methyl-4-[4N-(2-N-benzyl-N-methylamino)-3,4-dioxocyclobuten-1-yl)amino]phenyl-1,2,3,4-tetrahydroisoquinoline | | Water added to residue, extracted with ethyl acetate, variant c, MPRC in A), then crystallization from water | 158-162 |
| 39 | 6,8-dichloro-2-methyl-4(R)-[2N-(2-diethylamino-3,4-dioxocyclobuten-1-yl)amino]phenyl-1,2,3,4-tetrahydroisoquinoline | | Variant b, crystallization from ethyl acetate | 246-250 |
| 40 | 6,8-dichloro-2-methyl-4(R)-[2N-(2-N,N-dipropylamino)-3,4-dioxocyclobuten-1-yl)amino]phenyl-1,2,3,4-tetrahydroisoquinoline | | Variant c, MPRC in A), then crystallization from water | 190-194 |
| 41 | 6,8-dichloro-2-methyl-4(R)-[2N-(2-N-pyrrolidino-3,4-dioxocyclobuten-1-yl)amino]phenyl-1,2,3,4-tetrahydroisoquinoline | | Variant c, MPRC in A), then crystallization from water | 220-224 |

-continued

| Example | Name | Formula XIX | Reaction conditions | m.p. ° C. |
|---|---|---|---|---|
| 42 | 6,8-dichloro-2-methyl-4(R)-[2N-(2-N-methyl-N-isopropyl)amino-3,4-dioxocyclobuten-1-yl)amino]phenyl-1,2,3,4-tetrahydroisoquinoline | | Variant c, MPRC in A), then crystallization from water | 210-214 |
| 43 | 6,8-dichloro-2-methyl-4-[4N-(2-N-phenylamino-3,4-dioxocyclobuten-1-yl)amino]phenyl-1,2,3,4-tetrahydroisoquinoline | | Variant b, crystallization from ethyl acetate | 288-294 |
| 44 | 6,8-dichloro-2-methyl-4-[2N-(2-N-methylamino-3,4-dioxocyclobuten-1-yl)amino]phenyl-1,2,3,4-tetrahydroisoquinoline | | Variant c, MPRC in A), then crystallization from a little ethyl acetate | 224-230 |
| 45 | 6,8-dichloro-2-methyl-4-[2N-(2-N-(1-hexylamino)-3,4-dioxocyclobuten-1-yl)amino]phenyl-1,2,3,4-tetrahydroisoquinoline | | Variant c, MPRC in A), then crystallization from a little ethyl acetate | 157-160 |

-continued

| Example | Name | Formula XIX | Reaction conditions | m.p. ° C. |
|---|---|---|---|---|
| 46 | 6,8-dichloro-2-methyl-4-[2N-(2-N-isopropylamino-3,4-dioxocyclobuten-1-yl)amino]phenyl-1,2,3,4-tetrahydroisoquinoline | | Variant c, MPRC in A), then crystallization from a little ethyl acetate | 238-241 |
| 47 | 6,8-dichloro-2-methyl-4-[2N-(2-N-cyclopentylamino-3,4-dioxocyclobuten-1-yl)amino]phenyl-1,2,3,4-tetrahydroisoquinoline | | Variant a | 278-281 |
| 48 | 6,8-dichloro-2-methyl-4-[2N-(2N-(2-furylmethyl)amino-3,4-dioxocyclobuten-1-yl)amino]phenyl-1,2,3,4-tetrahydroisoquinoline | | Variant c, MPRC in A), then crystallization from a little ethyl acetate | 279-283 |
| 49 | 6,8-dichloro-2-methyl-4-[2N-(2-N-ethylamino-3,4-dioxocyclobuten-1-yl)amino]phenyl-1,2,3,4-tetrahydroisoquinoline | | Variant c, MPRC in A), then crystallization from a little ethyl acetate | 205-208 |

-continued

| Example | Name | Formula XIX | Reaction conditions | m.p. ° C. |
|---------|------|-------------|---------------------|-----------|
| 50 | 6,8-dichloro-2-methyl-4-[2N-(2-N-dimethylaminoethylamino-3,4-dioxocyclobuten-1-yl)amino]phenyl-1,2,3,4-tetrahydroisoquinoline | | Variant c, MPRC in A), then crystallization from a little ethyl acetate | 208-211 |
| 51 | 6,8-dichloro-2-methyl-4-[4N-(2-N-ethylamino-3,4-dioxocyclobuten-1-yl)amino]phenyl-1,2,3,4-tetrahydroisoquinoline | | Variant a | 292-297 |
| 52 | 6,8-dichloro-2-methyl-4-[2N-(2N-(3-picolyl-methyl)amino-3,4-dioxocyclobuten-1-yl)amino]phenyl-1,2,3,4-tetrahydroisoquinoline | | Variant c, MPRC in A), then crystallization from a little ethyl acetate | 244-246 |

-continued

| Example | Name | Formula XIX | Reaction conditions | m.p. °C. |
|---|---|---|---|---|
| 53 | 6,8-dichloro-2-methyl-4-[4N-(2N-methylamino-3,4-dioxocyclobuten-1-yl)amino]phenyl-1,2,3,4-tetrahydroisoquinoline | | Variant a | 328-334 |
| 54 | 6,8-dichloro-2-methyl-4-[4N-(2N-cyclopropylamino-3,4-dioxocyclobuten-1-yl)amino]phenyl-1,2,3,4-tetrahydroisoquinoline | | Variant a | 300-304 |
| 55 | 6,8-dichloro-2-methyl-4-[4N-(2N-isopropylamino-3,4-dioxocyclobuten-1-yl)amino]phenyl-1,2,3,4-tetrahydroisoquinoline | | Variant a | 268-272 |

| Example | Name | Formula XIX | Reaction conditions | m.p. ° C. |
|---|---|---|---|---|
| 56 | 6,8-dichloro-2-methyl-4-[4N-(2N-(2-furyl-methyl)amino-3,4-dioxocyclobuten-1-yl)amino]phenyl-1,2,3,4-tetrahydroisoquinoline | | Variant a | 264-268 |
| 57 | 6,8-dichloro-2-methyl-4-[4N-(2N-dimethylaminoethylamino)-3,4-dioxocyclobuten-1-yl)amino]phenyl-1,2,3,4-tetrahydroisoquinoline | | Variant a | 262-266 |
| 58 | 6,8-dichloro-2-methyl-4-[4N-(1-hexylamino)-3,4-dioxocyclobuten-1-yl)amino]phenyl-1,2,3,4-tetrahydroisoquinoline | | Variant a | 234-238 |

-continued

| Example | Name | Formula XIX | Reaction conditions | m.p. ° C. |
|---|---|---|---|---|
| 59 | 6,8-dichloro-2-methyl-4-[4N-(3-picolylamino)-3,4-dioxocyclobuten-1-yl)amino]phenyl-1,2,3,4-tetrahydroisoquinoline | | Variant a | 288-290 |
| 60 | 6,8-dichloro-2-methyl-4-[4N-2-methylamino-3,4-dioxocyclobuten-1-yl)amino]phenyl-1,2,3,4-tetrahydroisoquinoline | | Variant a | 295-298 |
| 61 | 6,8-dichloro-2-methyl-4-[4N-(2-ethylamino)-3,4-dioxocyclobuten-1-yl)amino]phenyl-1,2,3,4-tetrahydroisoquinoline | | Variant a | decomposition at 200° C. |
| 62 | 6,8-dichloro-2-methyl-4-[3N-(2-(2-furylmethylamino)-3,4-dioxocyclobuten-1-yl)amino]phenyl-1,2,3,4-tetrahydroisoquinoline | | Variant a | decomposition at 200° C. |

| Example | Name | Formula XIX | Reaction conditions | m.p. °C. |
|---|---|---|---|---|
| 63 | 6,8-dichloro-2-methyl-4-[3N-(2-cyclopentylamino-3,4-dioxocyclobuten-1-yl)amino]phenyl-1,2,3,4-tetrahydroisoquinoline | | Variant a | 248-252 |
| 64 | 6,8-dichloro-2-methyl-4-[3N-(2-isopropylamino)-3,4-dioxocyclobuten-1-yl)amino]phenyl-1,2,3,4-tetrahydroisoquinoline | | Variant a | 240-244 |
| 65 | 6,8-dichloro-2-methyl-4-[3N-(2N-dimethylaminoethylamino)-3,4-dioxocyclobuten-1-yl)amino]phenyl-1,2,3,4-tetrahydroisoquinoline | | Variant a | 198-200 |

Example 66: 6,8-Dichloro-2-methyl-4-[4-acetylamino-2-methylphenyl]-1,2,3,4-tetrahydroisoquinoline

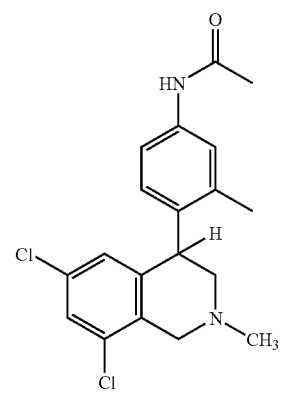

was obtained by dropwise addition of 0.4 ml of concentrated sulfuric acid (96%) to a solution of 125 mg of 1-(4-acetylamino-2-methylphenyl)-2-[N-(2,4-dichlorobenzyl)-N-methylamino]ethanol in 3 ml of anhydrous dichloromethane. The two-phase mixture was stirred at room temperature for 5 hours and then poured onto ice, made strongly alkaline with 2N aqueous NaOH and extracted several times with dichloromethane. Washing of the organic phase with water and drying over sodium sulfate were followed by removal of the solvent by distillation, chromatography of the residue on a silica gel column with a mixture of equal parts of ethyl acetate and toluene and renewed distillation of the solvent under reduced pressure in a rotavapor. Crystalline solid, m.p. 182-185° C.

Example 67

4-[4-Amino-2-methylphenyl]-6,8-dichloro-2-methyl-1,2,3,4-tetrahydroisoquinoline dihydrochloride

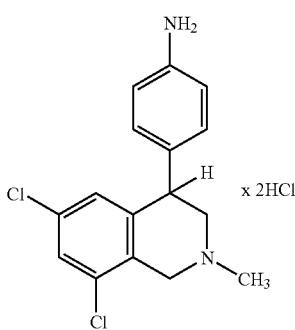

was obtained by boiling a suspension of 0.05 g of 6,8-dichloro-2-methyl-4-[4-acetylamino-2-methylphenyl]-1,2,3,4-tetrahydroisoquinoline (Example 66) in a mixture of 2 ml of water and 2 ml of concentrated hydrochloric acid for 2 hours and leaving to stand at room temperature overnight, resulting in a clear solution. Removal of the aqueous acid by distillation resulted in the bishydrochloride as colorless crystalline compound. m.p. (decomposition) 250-260° C.

The 6,8-dichloro-2-methyl-4-[4-amino-2-methylphenyl]-1,2,3,4-tetrahydroisoquinoline was obtained as free base by treating an aqueous solution of 6,8-dichloro-2-methyl-4-[4-amino-2-methylphenyl]-1,2,3,4-tetrahydroisoquinoline dihydrochloride with NaOH, by filtering off the precipitate, washing with water and drying. Amorphous solid with decomposition above 70° C.

Example 68

6,8-Dichloro-2-methyl-4-[4N-(2-ethoxy-3,4-dioxocyclobuten-1-yl)amino-2-methylphenyl]-1,2,3,4-tetrahydroisoquinoline

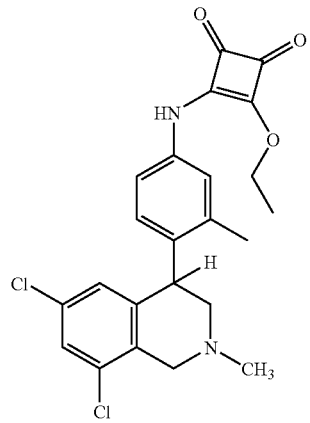

110 mg of 1,2-diethoxy-3,4-dioxo-1-cyclobuten (diethyl squarate) were added to a solution of 0.2 g of 4-[4-amino-2-methylphenyl]-6,8-dichloro-2-methyl-1,2,3,4-tetrahydroisoquinoline dihydrochloride in 15 ml of anhydrous ethanol and, after stirring at room temperature for 20-25 hours, the precipitate was filtered off. Colorless crystalline solid, m.p.: 235-240° C.

Example 69

4-[4N-(2-Amino-3,4-dioxocyclobuten-1-yl)amino-2-methyl-phenyl]-6,8-dichloro-2-methyl-1,2,3,4-tetrahydroisoquinoline

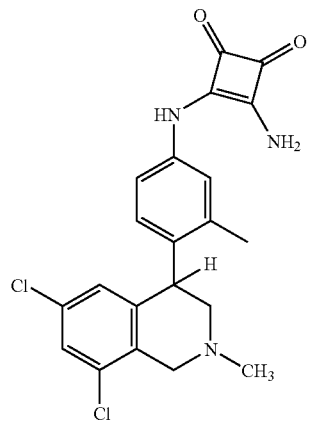

was obtained by adding 4 ml of a saturated solution of ammonia in methanol to a suspension of 100 mg of 6,8-dichloro-2-methyl-4-[4N-(2-ethoxy-3,4-dioxocyclobuten-1-yl)amino-2-methylphenyl]-1,2,3,4-tetrahydroisoquinoline (Example 68). After stirring at room temperature for 5 hours and leaving to stand overnight, the crystals were filtered off and washed with methanol. m.p. 315-318° C.

Example 70

6,8-Dichloro-2-methyl-4-[4N-(2N-methyl-2N-propylamino-3,4-dioxocyclobuten-1-yl)amino-2-methylphenyl]-1,2,3,4-tetrahydroisoquinoline

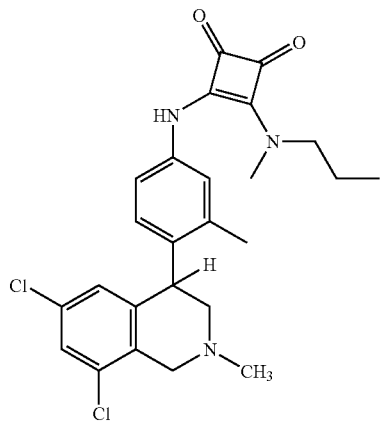

was obtained in analogy to the method indicated in Example 16 from 6,8-dichloro-2-methyl-4-[4N-(2-ethoxy-3,4-dioxocyclobuten-1-yl)amino-2-methylphenyl]-1,2,3,4-tetrahydroisoquinoline and N-1-propyl-N-methylamine. Crystalline solid, m.p. 158-163° C.

Example 71

6,8-Dichloro-2-methyl-4-[4N-(2N-methylamino-3,4-dioxocyclobuten-1-yl)amino-2-methylphenyl]-1,2,3,4-tetrahydroisoquinoline

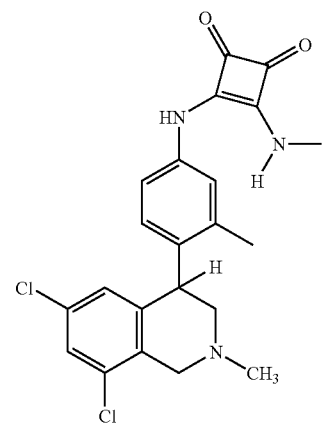

was obtained in analogy to the method indicated in Example 16 from 6,8-dichloro-2-methyl-4-[4N-(2-ethoxy-3,4-dioxocyclobuten-1-yl)amino-2-methylphenyl]-1,2,3,4-tetrahydroisoquinoline and methylamine. Crystalline solid, m.p. >310° C.

Example 72

6,8-Dichloro-2-methyl-4(R)-[3N-(2-methylamino-3,4-dioxocyclobuten-1-yl)amino]phenyl-1,2,3,4-tetrahydroisoquinoline

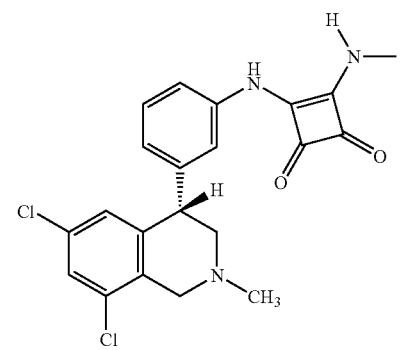

was obtained in analogy to the method indicated in Example 16 from 6,8-dichloro-2-methyl-4(S)-[3N-(2-ethoxy-3,4-dioxocyclobuten-1-yl)amino]-phenyl-1,2,3,4-tetrahydroisoquinoline (Example 5) and methylamine. Crystalline solid, m.p. >310° C.

Example 73

6,8-Dichloro-2-methyl-4(R)-[2N-(2-methylamino-3,4-dioxo-cyclobuten-1-yl)amino]phenyl-1,2,3,4-tetrahydroisoquinoline

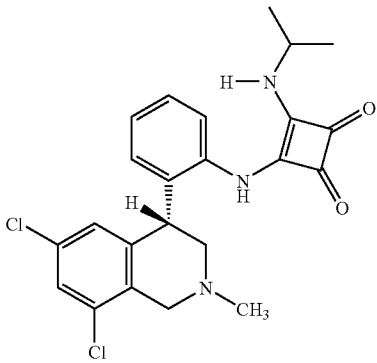

was obtained in analogy to the method indicated in Example 16 from 6,8-dichloro-2-methyl-4(R)-[2N-(2-ethoxy-3,4-dioxocyclobuten-1-yl)amino]-phenyl-1,2,3,4-tetrahydroisoquinoline (Example 6) and isopropylamine. Crystalline solid, m.p. 268-270° C.

Example 74

6,8-Dichloro-2-methyl-4(R)-[2N-(2-methylamino-3,4-dioxo-cyclobuten-1-yl)amino]phenyl-1,2,3,4-tetrahydroisoquinoline

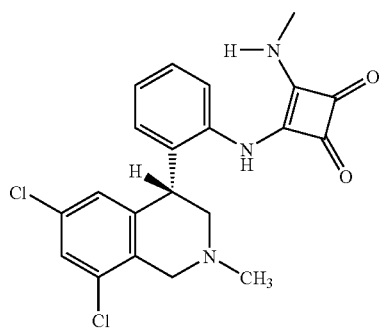

was obtained in analogy to the method indicated in Example 16 from 6,8-dichloro-2-methyl-4(R)-[2N-(2-ethoxy-3,4-dioxocyclobuten-1-yl)amino]-phenyl-1,2,3,4-tetrahydroisoquinoline (Example 6) and methylamine. Crystalline solid, m.p. 265° C.

Pharmacological Data:

Assay: Determination of the NHE-Inhibitory Effect

In this assay, the recovery of the intracellular pH ($pH_i$) after an acidification which occurs even under bicarbonate-free conditions with functional NHE was determined. To this end, the $pH_i$ was determined using the pH-sensitive fluorescent dye BCECF (calbiochem, the precursor BCECF-AM was employed). The cells were initially loaded with BCECF. The BCECF fluorescence was determined in a ratio fluorescence spectrometer (Photon Technology International, South Brunswick, N.J., USA) with excitation wavelengths of 505 and 440 nm and an emission wavelength of 535 nm and converted into the $pH_i$ using calibration plots. The cells had been incubated in $NH_4Cl$ buffer (pH 7.4) for the BCECF loading ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 was adjusted with 1 M NaOH). The intracellular acidification was induced by adding 975 µl of an $NH_4Cl$-free buffer (see below) to 25 µl aliquots of the cells incubated in $NH_4Cl$ buffer. The subsequent rate of pH recovery was recorded for two minutes with NHE1, five minutes with NHE2 and three minutes with NHE3. To calculate the inhibitory power of the tested substances, the cells were initially investigated in buffers with which there was complete or absolutely no pH recovery. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 was adjusted with 1 M NaOH). To determine the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, a pH of 7.0 was adjusted with 1 M NaOH). The substances to be tested were made up in the $Na^+$-containing buffer. The recovery of the intracellular pH at each tested concentration of a substance was expressed as a percentage of the maximum recovery. The $IC_{50}$ of the respective substance for the individual NHE subtypes was calculated from the percentages of pH recovery using the Sigma Plot program.

| Example | IC50 (µM) |
|---|---|
| 18 | 0.26 |
| 19 | 1.15 |
| 22 | 0.0985 |
| 23 | 0.31 |
| 24 | 2.49 |
| 25 | 2.81 |
| 26 | 1.70 |
| 27 | 0.21 |
| 28 | 0.26 |
| 29 | 7.14 |
| 30 | 0.14 |
| 31 | 0.13 |
| 32 | 0.68 |
| 33 | 0.031 |
| 34 | 0.052 |
| 36 | 0.23 |
| 37 | 0.85 |
| 38 | 8.0 |
| 39 | 1.52 |
| 40 | 0.24 |
| 41 | 0.11 |
| 42 | 0.15 |

What is claimed is:

1. A compound of formula I

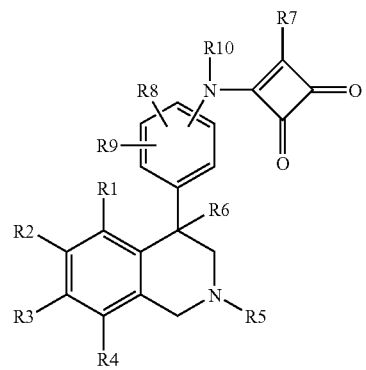

wherein:
R1, R2, R3 and R4 are independently hydrogen, F, Cl, Br, I, CN, $NO_2$, or R11-$(C_mH_{2m})$-$A_n$-;
m is zero, 1, 2, 3 or 4;
n is zero or 1;
R11 is hydrogen, methyl, $C_pF_{2p+1}$ or phenyl;
p is 1, 2 or 3;
A is oxygen, NH, N($CH_3$) or S(O)$_q$;
q is zero, 1 or 2;
R5 is hydrogen, an alkyl having 1, 2, 3, 4, 5 or 6 carbon atoms which may be partially or completely fluorinated, or cycloalkyl having 3, 4, 5 or 6 carbon atoms;
R6 is hydrogen, OH, F, $CF_3$, methyl, ethyl, isopropyl or cyclopropyl;
R7 is hydrogen, an alkyl having 1, 2, 3, 4, 5 or 6 carbon atoms, cycloalkyl having 3, 4, 5 or 6 carbon atoms, OR12 or NR13R14;
R12 is hydrogen, an alkyl having 1, 2, 3, 4, 5 or 6 carbon atoms which may be partially or completely fluorinated, or cycloalkyl having 3, 4, 5 or 6 carbon atoms;

R13 and R14 are independently hydrogen, cycloalkyl having 3, 4, 5 or 6 carbon atoms, alkyl having 1, 2, 3, 4, 5 or 6 carbon atoms which may be partly or completely fluorinated, phenyl, phenylalkyl having 1, 2 or 3 carbon atoms in the alkyl moiety, heteroaryl or heteroarylmethyl, wherein the phenyl and heteroaryl radicals are un-substituted or substituted by 1, 2, 3, 4 or 5 substituents selected from the group consisting of fluorine, chlorine, methyl, $CF_3$, methoxy and OH; and wherein the alkyl radicals are un-substituted or are substituted by 1, 2 or 3 substituents selected from the group consisting of alkoxy having 1, 2, 3 or 4 carbon atoms, NR15R16 and cycloalkyl having 3, 4, 5 or 6 carbon atoms, or R13 and R14 taken together with the nitrogen atom to which they are attached form a 3, 4, 5, 6, 7, 8 or 9-membered ring, wherein one carbon atom of the ring may be replaced by an oxygen atom or an $NCH_3$ group;

R15 and R16 are independently hydrogen or alkyl having 1, 2, 3 or 4 carbon atoms;

R8 and R9 are independently hydrogen, F, Cl, OH, $CH_3$, $CH_3O$, $CF_3$, $CF_3CH_2O$ or $CH_3SO_2$; and R10 is hydrogen, methyl or ethyl;

or a pharmaceutically acceptable salt or trifluoroacetate thereof.

2. The compound according to claim 1, wherein

R1, R2, R3 and R4 are hydrogen, F, Cl, Br, CN or R11-$(C_mH_{2m})$-$A_n$-;

m is zero or 1;

p is 1 or 2;

A is oxygen or $S(O)_q$;

R5 is hydrogen, methyl, ethyl or cyclopropyl;

R6 is hydrogen or methyl;

R7 is OR12 or NR13R14;

R12 is hydrogen or alkyl having 1, 2 or 3 carbon atoms;

R13 and R14 are independently hydrogen, alkyl having 1, 2, 3, 4, 5 or 6 carbon atoms which may be partly or completely fluorinated, cycloalkyl having 3, 4, 5 or 6 carbon atoms, phenyl, phenylalkyl having 1, 2 or 3 carbon atoms in the alkyl moiety, heteroaryl or heteroarylmethyl, wherein the phenyl and heteroaryl radicals are unsubstituted or are substituted by 1, 2, 3, 4 or 5 substituents selected from the group consisting of fluorine, chlorine, methyl, $CF_3$, methoxy and OH; and wherein the alkyl radicals are un-substituted or are substituted by 1, 2 or 3 substituents selected from the group consisting of alkoxy having 1, 2, 3 or 4 carbon atoms, NR15R16 and cycloalkyl having 3, 4, 5 or 6 carbon atoms, or R13 and R14 taken together with the nitrogen atom which they are attached form a 3, 4, 5, 6, 7 or 8-membered carbon ring, wherein one carbon atom of the ring may be replaced by an oxygen atom or an $NCH_3$ group;

R8 and R9 are hydrogen, F, Cl or $CH_3$; and

R10 is hydrogen or methyl;

or a pharmaceutically acceptable salt or trifluoroacetate thereof.

3. The compound according to claim 2 wherein:

R1 and R3 are hydrogen;

R2 and R4 are independently hydrogen or Cl; and

R5 is hydrogen, methyl or ethyl;

or a pharmaceutically acceptable salt or trifluoroacetate thereof.

4. The compound according to claim 1 selected from the group consisting of:

6,8-dichloro-2-methyl-4-[4N-(2-ethoxy-3,4-dioxocyclobuten-1-yl)amino]phenyl-1,2,3,4-tetrahydroisoquinoline, 6,8-dichloro-2-methyl-4-[3N-(2-ethoxy-3,4-dioxocyclobuten-1-yl)amino]phenyl-1,2,3,4-tetrahydroisoquinoline, 6,8-dichloro-2-methyl-4-[2N-(2-ethoxy-3,4-dioxocyclobuten-1-yl)amino]phenyl-1,2,3,4-tetrahydroisoquinoline, 6,8-dichloro-2-methyl-4(S)-[4N-(2-ethoxy-3,4-dioxocyclobuten-1-yl)amino]phenyl-1,2,3,4-tetrahydroisoquinoline, 6,8-dichloro-2-methyl-4(S)-[3N-(2-ethoxy-3,4-dioxocyclobuten-1-yl)amino]phenyl-1,2,3,4-tetrahydroisoquinoline, 6,8-dichloro-2-methyl-4(R)-[2N-(2-ethoxy-3,4-dioxocyclobuten-1-yl)amino]phenyl-1,2,3,4-tetrahydroisoquinoline, 6,8-dichloro-2-methyl-4-[4N-(2-hydroxy-3,4-dioxocyclobuten-1-yl)amino]phenyl-1,2,3,4-tetrahydroisoquinoline, 6,8-dichloro-2-methyl-4-[3N-(2-hydroxy-3,4-dioxocyclobuten-1-yl)amino]phenyl-1,2,3,4-tetrahydroisoquinoline, 6,8-dichloro-2-methyl-4-[2N-(2-hydroxy-3,4-dioxocyclobuten-1-yl)amino]phenyl-1,2,3,4-tetrahydroisoquinoline, 6,8-dichloro-2-methyl-4-[4N-(2-amino-3,4-dioxocyclobuten-1-yl)amino]phenyl-1,2,3,4-tetrahydroisoquinoline, 6,8-dichloro-2-methyl-4-[3N-(2-amino-3,4-dioxocyclobuten-1-yl)amino]phenyl-1,2,3,4-tetrahydroisoquinoline, 6,8-dichloro-2-methyl-4-[2N-(2-amino-3,4-dioxocyclobuten-1-yl)amino]phenyl-1,2,3,4-tetrahydroisoquinoline, 6,8-dichloro-2-methyl-4(S)-[4N-(2-amino-3,4-dioxocyclobuten-1-yl)amino]phenyl-1,2,3,4-tetrahydroisoquinoline, 6,8-dichloro-2-methyl-4(S)-[3N-(2-amino-3,4-dioxocyclobuten-1-yl)amino]phenyl-1,2,3,4-tetrahydroisoquinoline, 6,8-dichloro-2-methyl-4(S)-[2N-(2-amino-3,4-dioxocyclobuten-1-yl)amino]phenyl-1,2,3,4-tetrahydroisoquinoline, 6,8-dichloro-2-methyl-4-[4N-(2-N-cyclohexyl-N-methylamino-3,4-dioxocyclobuten-1-yl)amino]phenyl-1,2,3,4-tetrahydroisoquinoline, 6,8-dichloro-2-methyl-4-[4N-(2-dimethylamino-3,4-dioxocyclobuten-1-yl)amino]phenyl-1,2,3,4-tetrahydroisoquinoline, 6,8-dichloro-2-methyl-4-[3N-(2-dimethylamino-3,4-dioxocyclobuten-1-yl)amino]phenyl-1,2,3,4-tetrahydroisoquinoline, 6,8-dichloro-2-methyl-4(S)-[4N-(2-dimethylamino-3,4-dioxocyclobuten-1-yl)amino]phenyl-1,2,3,4-tetrahydroisoquinoline, 6,8-dichloro-2-methyl-4(R)-[2N-(2-dimethylamino-3,4-dioxocyclobuten-1-yl)amino]phenyl-1,2,3,4-tetrahydroisoquinoline, 6,8-dichloro-2-methyl-4(S)-[3N-(2-dimethylamino-3,4-dioxocyclobuten-1-yl)amino]phenyl-1,2,3,4-tetrahydroisoquinoline, 6,8-dichloro-2-methyl-4(S)-[4N-(2-N-(1-butyl)-N-methylamino-3,4-dioxocyclobuten-1-yl)amino]phenyl-1,2,3,4-tetrahydroisoquinoline, 6,8-dichloro-2-methyl-4-[4N-(2-dipropylamino-3,4-dioxocyclobuten-1-yl)amino]phenyl-1,2,3,4-tetrahydroisoquinoline, 6,8-dichloro-2-methyl-4-[4N-(2-(N-isobutyl-N-methylamino)-3,4-dioxocyclobuten-1-yl)amino]phenyl-1,2,3,4-tetrahydroisoquinoline, 6,8-dichloro-2-methyl-4-[4N-(2-(N-methoxyethyl)-N-methylamino)-3,4-dioxocyclobuten-1-yl)amino]phenyl-1,2,3,4-tetrahydroisoquinoline, 6,8-dichloro-2-methyl-4(S)-[4N-(2-diethylamino-3,4-dioxocyclobuten-1-yl)amino]phenyl-1,2,3,4-tetrahydroisoquinoline, 6,8-dichloro-2-methyl-4(S)-[4N-(2-(N-isopropyl-N-methylamino)-3,4-dioxocyclobuten-1-yl)amino]phenyl-1,2,3,4-tetrahydroisoquinoline, 6,8-dichloro-2-methyl-4-[N-(2-(N-cyclopropylmethyl-N-propylamino)-3,4-dioxocyclobuten-1-yl)amino]phenyl-1,2,3,4-tetrahydroisoquinoline, 6,8-dichloro-2-methyl-4(S)-[3N-(2-diethylamino-3,4-dioxocyclobuten-1-yl)amino]phenyl-1,2,3,4-tetrahydroisoquinoline, 6,8-dichloro-2-methyl-4(S)-[3N-(2-N-methyl-N-isopropyl)amino-3,4-dioxocyclobuten-1-yl)amino]phenyl-1,2,3,4-tetrahydroisoquinoline, 6,8-dichloro-2-methyl-4(S)-[4N-(2N-ethyl-N-isopropyl)amino-3,4-dioxocyclobuten-1-yl)amino]phenyl-1,2,3,4-tetrahydroisoquinoline, 6,8-dichloro-2-methyl-4(S)-[3N-(2-N-methyl-N-propyl)amino-3,4-dioxocyclobuten-1-yl)amino]phenyl-1,2,3,4-tetrahydroisoquinoline, 6,8-dichloro-2-methyl-4(S)-[3N-(2-N-pyrrolidino-3,4-dioxocyclobuten-1-yl)amino]phenyl-1,2,3,4-tetrahydroisoquinoline, 6,8-dichloro-2-methyl-4(S)-[4N-(2-N-cyclopropylamino)-3,4-dioxocyclobuten-1-yl)amino]phenyl-1,2,3,4-tetrahydroisoquinoline, 6,8-dichloro-2-methyl-4(S)-[4N-(2-N-pyrrolidino-3,4-dioxocyclobuten-1-yl)amino]phenyl-1,2,3,4-tetrahydroisoquinoline, 6,8-dichloro-2-methyl-4(R)-[2N-(2-N-methyl-N-propylamino)-3,4-dioxocyclobuten-1-yl)amino]phenyl-1,2,3,4-tetrahydroisoquinoline, 6,8-dichloro-2-methyl-4-[4N-(2-N-benzyl-N-methylamino)-3,4-dioxocyclobuten-1-yl)amino]phenyl-1,2,3,4-tetrahydroisoquinoline, 6,8-dichloro-2-methyl-4(R)-[2N-(2-diethylamino-3,4-dioxocyclobuten-1-yl)amino]phenyl-1,2,3,4-tetrahydroisoquinoline, 6,8-dichloro-2-methyl-4(R)-[2N-(2-dipropylamino)-3,4-dioxocyclobuten-1-yl)amino]phenyl-1,2,3,4-tetrahydroisoquinoline, 6,8-dichloro-2-methyl-4(R)-[2N-(2-N-pyrrolidino-3,4-dioxocyclobuten-1-yl)amino]phenyl-1,2,3,4-tetrahydroisoquinoline, 6,8-dichloro-2-methyl-4(R)-[2N-(2-N-methyl-N-isopropyl)amino-3,4-dioxocyclobuten-1-yl)amino]phenyl-1,2,3,4-tetrahydroisoquinoline, 6,8-dichloro-2-methyl-4-[4N-(2-N-phenylamino-3,4-dioxocyclobuten-1-yl)amino]phenyl-1,2,3,4-tetrahydroisoquinoline, 6,8-dichloro-2-methyl-4-[2N-(2-N-methylamino-3,4-dioxocyclobuten-1-yl)amino]phenyl-1,2,3,4-tetrahydroisoquinoline, 6,8-dichloro-2-methyl-4-[2N-(2-N-(1-hexylamino)-3,4-dioxocyclobuten-1-yl)amino]phenyl-1,2,3,4-tetrahydroisoquinoline, 6,8-dichloro-2-methyl-4-[2N-(2-N-isopropylamino-3,4-dioxocyclobuten-1-yl)amino]phenyl-1,2,3,4-tetrahydroisoquinoline, 6,8-dichloro-2-methyl-4-[2N-(2-N-cyclopentylamino-3,4-dioxocyclobuten-1-yl)amino]phenyl-1,2,3,4-tetrahydroisoquinoline, 6,8-dichloro-2-methyl-4-[2N-(2N-(2-furylmethyl)amino-3,4-dioxocyclobuten-1-yl)amino]phenyl-1,2,3,4-tetrahydroisoquinoline, 6,8-dichloro-2-methyl-4-[2N-(2-N-ethylamino-3,4-dioxocyclobuten-1-yl)amino]phenyl-1,2,3,4-tetrahydroisoquinoline, 6,8-dichloro-2-methyl-4-[2N-(2-N-dimethylaminoethylamino-3,4-dioxocyclobuten-1-yl)amino]phenyl-1,2,3,4-tetrahydroisoquinoline, 6,8-dichloro-2-methyl-4-[4N-(2-N-ethylamino-3,4-dioxocyclobuten-1-yl)amino]phenyl-1,2,3,4-tetrahydroisoquinoline, 6,8-dichloro-2-methyl-4-[2N-(2N-(3-picolylmethyl)amino-3,4-dioxocyclobuten-1-yl)amino]phenyl-1,2,3,4-tetrahydroisoquinoline, 6,8-dichloro-2-methyl-4-[4N-(2N-methylamino-3,4-dioxocyclobuten-1-yl)amino]phenyl-1,2,3,4-tetrahydroisoquinoline, 6,8-dichloro-2-methyl-4-[4N-(2N-cyclopropylamino-3,4-dioxocyclobuten-1-yl)amino]phenyl-1,2,3,4-tetrahydroisoquinoline, 6,8-dichloro-2-methyl-4-[4N-(2N-isopropylamino-3,4-dioxocyclobuten-1-yl)amino]phenyl-1,2,3,4-tetrahydroisoquinoline, 6,8-dichloro-2-methyl-4-[4N-(2N-(2-furylmethyl)amino-3,4-dioxocyclobuten-1-yl)amino]phenyl-1,2,3,4-tetrahydroisoquinoline, 6,8-dichloro-2-methyl-4-[4N-(2N-dimethylaminoethylamino)-3,4-dioxocyclobuten-1-yl)amino]phenyl-1,2,3,4-tetrahydroisoquinoline, 6,8-dichloro-2-methyl-4-[4N-(1-hexylamino)-3,4-dioxocyclobuten-1-yl)amino]phenyl-1,2,3,4-tetrahydroisoquinoline, 6,8-dichloro-2-methyl-4-[4N-(2-picolylamino)-3,4-dioxocyclobuten-1-yl)amino]phenyl-1,2,3,4-tetrahydroisoquinoline, 6,8-dichloro-2-methyl-4-[4N-(2N-methylamino-3,4-dioxocyclobuten-1-yl)amino]phenyl-1,2,3,4-tetrahydroisoquinoline, 6,8-dichloro-2-methyl-4-[4N-(2-ethylamino)-3,4-dioxocyclobuten-1-yl)amino]phenyl-1,2,3,4-tetrahydroisoquinoline, 6,8-dichloro-2-methyl-4-[3N-(2-(2-furylmethylamino)-3,4-dioxocyclobuten-1-yl)amino]phenyl-1,2,3,4-tetrahydroisoquinoline, 6,8-dichloro-2-methyl-4-[3N-(2-cyclopentylamino-3,4-dioxocyclobuten-1-yl)amino]phenyl-1,2,3,4-tetrahydroisoquinoline, 6,8-dichloro-2-methyl-4-[3N-(2-isopropylamino)-3,4-dioxocyclobuten-1-yl)amino]phenyl-1,2,3,4-tetrahydroisoquinoline, 6,8-dichloro-2-methyl-4-[3N-(2N-dimethylaminoethylamino)-3,4-dioxocyclobuten-1-yl)amino]phenyl-1,2,3,4-tetrahydroisoquinoline, 6,8-dichloro-2-methyl-4(R)-[2N-(2-isopropylamino-3,4-dioxocyclobuten-1-yl)amino]phenyl-1,2,3,4-tetrahydroisoquinoline, 6,8-dichloro-2-methyl-4(R)-[3N-(2-methylamino-3,4-dioxocyclobuten-1-yl)amino]phenyl-1,2,3,4-tetrahydroisoquinoline, and 6,8-dichloro-2-methyl-4(R)-[2N-(2-methylamino-3,4-dioxocyclobuten-1-yl)amino]phenyl-1,2,3,4-tetrahydroisoquinoline, or a pharmaceutically acceptable salt or trifluoroacetate thereof.

5. A pharmaceutical composition comprising the compound according to claim 1 or a pharmaceutically acceptable salt thereof, in combination with a pharmaceutically acceptable excipient.

6. A pharmaceutical composition comprising the compound according to claim 2 or a pharmaceutically acceptable salt thereof, in combination with a pharmaceutically acceptable excipient.

7. A pharmaceutical composition comprising the compound according to claim 3 or a pharmaceutically acceptable salt thereof, in combination with a pharmaceutically acceptable excipient.

8. A pharmaceutical composition comprising the compound according to claim 4 or a pharmaceutically acceptable salt thereof, in combination with a pharmaceutically acceptable excipient.

* * * * *